(12) United States Patent
Hitchcock

(10) Patent No.: US 12,220,331 B1
(45) Date of Patent: Feb. 11, 2025

(54) BI-DIRECTIONAL ADJUSTABLE PROSTHETIC LIMB CONNECTION WITH LINEAR ADJUSTABILITY

(71) Applicant: JERMEC Engineering, LLC, Mesa, AZ (US)

(72) Inventor: Michael Hitchcock, Mesa, AZ (US)

(73) Assignee: JERMEC Engineering, LLC, Mesa, AZ (US)

( * ) Notice: Subject to any disclaimer, the term of this patent is extended or adjusted under 35 U.S.C. 154(b) by 0 days.

(21) Appl. No.: 18/747,781

(22) Filed: Jun. 19, 2024

Related U.S. Application Data

(63) Continuation-in-part of application No. 18/621,453, filed on Mar. 29, 2024.

(51) Int. Cl.
*A61F 2/76* (2006.01)
*A61F 2/80* (2006.01)
*A61F 2/50* (2006.01)

(52) U.S. Cl.
CPC ............. *A61F 2/80* (2013.01); *A61F 2/76* (2013.01); *A61F 2002/5021* (2013.01)

(58) Field of Classification Search
CPC ...... A61F 2/54; A61F 2/76; A61F 2/78; A61F 2/80; A61F 2002/5016; A61F 2002/5021; A61F 2002/7875
See application file for complete search history.

(56) References Cited

U.S. PATENT DOCUMENTS

| | | | | |
|---|---|---|---|---|
| 2005/0027371 | A1* | 2/2005 | Chen | A61F 2/76 623/38 |
| 2012/0259433 | A1* | 10/2012 | Dillingham | A61F 2/78 623/36 |
| 2021/0338459 | A1* | 11/2021 | Tompkins | A61F 2/80 |

FOREIGN PATENT DOCUMENTS

| | | | | |
|---|---|---|---|---|
| GB | 2173569 A | * | 10/1986 | A61F 2/76 |
| WO | WO-2013090733 A1 | * | 6/2013 | A61F 2/60 |
| WO | WO-2014160865 A1 | * | 10/2014 | A61F 2/80 |

OTHER PUBLICATIONS

Advanced Trans-tibial Socket Fabrication Using Selective Laser Sintering (Year: 2007).*

\* cited by examiner

*Primary Examiner* — Christie Bahena
(74) *Attorney, Agent, or Firm* — Kenneth C. Booth; Booth Udall Fuller, PLC

(57) ABSTRACT

An adjustable prosthetic limb connection with a mounting plate, an alignment mechanism, and a lower connector. The mounting plate is configured to attach to a prosthetic limb socket, the alignment mechanism is configured to couple with the mounting plate, and the lower connector is configured to attach to the alignment mechanism and to a prosthetic limb. The alignment mechanism is configured to allow adjustment of the alignment of the lower connector with respect to the mounting plate with at least two linear degrees of freedom. The alignment mechanism may comprise a base plate and a linear slide. The base plate is configured to be secured against the mounting plate and may have first and second rows of teeth. The linear slide may be positioned between the base plate and the mounting plate and may have first and second ridges configured to interface with the first and second rows of teeth.

20 Claims, 31 Drawing Sheets

| | | LINEAR SLIDE PER QUADRANT CENTER POST OFFSET POSITIONS | | | | | | |
|---|---|---|---|---|---|---|---|---|
| | mm | | | | | | | |
| F | 11 | F1 | F2 | F3 | F4 | F5 | | |
| E | 8.8 | E1 | E2 | E3 | E4 | E5 | E6 | |
| D | 6.6 | D1 | D2 | D3 | D4 | D5 | D6 | |
| C | 4.4 | C1 | C2 | C3 | C4 | C5 | C6 | |
| B | 2.2 | B1 | B2 | B3 | B4 | B5 | B6 | |
| A | 0 | A1 | A2 | A3 | A4 | A5 | A6 | |
| | | 0 | 2.2 | 4.4 | 6.6 | 8.8 | 11 | mm |
| | | 1 | 2 | 3 | 4 | 5 | 6 | |

FIG. 31

BI-DIRECTIONAL ADJUSTABLE PROSTHETIC LIMB CONNECTION WITH LINEAR ADJUSTABILITY

RELATED APPLICATIONS

This application is a continuation-in-part of U.S. non-provisional patent application Ser. No. 18/621,453, filed Mar. 29, 2024 to Michael Hitchcock, titled "BI-DIRECTIONAL ADJUSTABLE PROSTHETIC LIMB CONNECTION," the entirety of the disclosure of which is hereby incorporated by this reference.

TECHNICAL FIELD

This document relates to a prosthetic limb connection, and more specifically to a bi-directional adjustable prosthetic limb connection with at least two linear degrees of freedom.

BACKGROUND

For amputees, the socket into which their residual limb is inserted is typically custom-made and completely unique to the amputee and the amputee's physiology. Because of that uniqueness, the line of force from the distal end of the socket to the ground does not necessarily line up with the center of the socket. Thus, adjustments must be made to correctly place the line of force. Currently, to accomplish this, doctors typically start with multiple iterations using single direction adjustments to discover whether two directions of adjustment in the transverse plane are required to restore the amputee to previous levels of mobility and activity with minimal discomfort. However, to get the correct pressure on the weight bearing parts of the amputee's residual limb, the line of force frequently requires adjustment in two directions of the transverse plane at the same time.

After the iterations using single direction adjustments have determined that two directions of adjustment are needed, over several visits back to the medical provider, then adjustments are made in multiple directions. However, it frequently takes multiple iterations and visits with an initial test socket, then at least one other iteration with a completely new test socket, which is followed by a new definitive socket. Thus, the process for fitting an amputee with a prosthetic is cumbersome, extremely time-consuming, and has an increased cost due to multiple iterations. The time and money cost of providing comfort and mobility using conventional technologies is excessive. Additionally, many of the components used to make the adjustments are fixed in the amount of offset they provide in the transverse plane. This often leads to the situation where the adjustment provided is "better" but may not be optimum for the amputee.

SUMMARY

Aspects of this document relate to an adjustable prosthetic limb connection, comprising a mounting plate configured to attach to a prosthetic limb socket of a user, an alignment mechanism configured to attach to the mounting plate, the alignment mechanism comprising a base plate having a base plate aperture extending through the base plate, wherein the base plate aperture has a plurality of grooves extending outward around a top inner edge of the base plate, wherein the base plate is configured to attach to the mounting plate, an outer cam configured to sit within the base plate aperture, the outer cam having an outer cam aperture extending through the outer cam and an outer lip extending outward around a top outer edge of the outer cam, wherein the outer lip has a plurality of ridges positioned around the top outer edge of the outer cam, wherein the plurality of ridges of the outer lip is configured to interlock with the plurality of grooves of the base plate when the outer cam is positioned within the base plate to fix a rotational position of the outer cam with respect to the base plate, and wherein the outer cam aperture has a plurality of grooves extending outward around a top inner edge of the outer cam, and wherein the outer cam aperture is offset from a center of the outer cam, and a center cam configured to sit within the outer cam aperture, the center cam having a center cam aperture offset from a center of the center cam and a center lip extending outward around a top outer edge of the center cam, wherein the center lip has a plurality of ridges positioned around the top outer edge of the center cam, wherein the plurality of ridges of the center lip is configured to interlock with the plurality of grooves of the outer cam when the center cam is positioned within the outer cam to fix a rotational position of the center cam with respect to the outer cam, wherein the base plate is configured to hold the outer cam and the center cam against the mounting plate such that the center cam is maintained within the outer cam and the outer cam is maintained within the base plate, a lower connector configured to align with the center cam aperture of the center cam and attach to a prosthetic limb, and a fastener configured to extend through the lower connector and threadedly couple with the center cam aperture of the center cam to couple the lower connector to the center cam, wherein the alignment mechanism is configured to allow adjustment of the alignment of the lower connector with respect to the mounting plate.

Particular embodiments may comprise one or more of the following features. The lower connector may have an upper surface configured to interface with the center cam and rotationally fix the lower connector with respect to the center cam. The lower connector may comprise a base and a main body, wherein the bottom surface of the base is configured to interface with the upper surface of the main body to rotationally fix the main body with respect to the base. Each of the bottom surface of the base and the upper surface of the main body may have a plurality of radial ridges and the pluralities of radial ridges on the bottom surface of the base and the upper surface of the main body may allow a rotational position of the main body with respect to the base to be adjusted.

Aspects of this document relate to an adjustable prosthetic limb connection, comprising a mounting plate configured to attach to a prosthetic limb socket of a user, an alignment mechanism configured to attach to the mounting plate, the alignment mechanism comprising a base plate having a base plate aperture extending through the base plate, an outer cam configured to sit within the base plate aperture, wherein when the outer cam sits within the base plate aperture, a rotational position of the outer cam with respect to the base plate is fixed, the outer cam having an outer cam aperture extending through the outer cam offset from a center of the outer cam, and a center cam configured to sit within the outer cam aperture, wherein when the center cam sits within the outer cam aperture, a rotational position of the center cam with respect to the outer cam is fixed, the center cam having a center cam aperture offset from a center of the center cam, and a lower connector configured to couple with the center cam aligned with the center cam aperture, wherein the alignment mechanism is configured to allow adjustment of the alignment of the lower connector with respect to the mounting plate.

Particular embodiments may comprise one or more of the following features. The lower connector may have an upper surface configured to interface with the center cam and rotationally fix the lower connector with respect to the center cam. The lower connector may comprise a base and a main body and the bottom surface of the base may be configured to interface with the upper surface of the main body to rotationally fix the main body with respect to the base. Each of the bottom surface of the base and the upper surface of the main body may have a plurality of radial ridges and the pluralities of radial ridges on the bottom surface of the base and the upper surface of the main body may allow a rotational position of the main body with respect to the base to be adjusted. The base plate may be configured to attach to the mounting plate and hold the outer cam and the center cam against the mounting plate such that the center cam is maintained within the outer cam and the outer cam is maintained within the base plate. The outer cam may have an outer lip extending outward around a top outer edge of the outer cam and the outer lip may be configured to interlock with the base plate when the outer cam is positioned within the base plate to fix the rotational position of the outer cam with respect to the base plate. The center cam may have a center lip extending outward around a top outer edge of the center cam and the center lip may be configured to interlock with the outer cam when the center cam is positioned within the outer cam to fix the rotational position of the center cam with respect to the outer cam.

Aspects of this document relate to an adjustable prosthetic limb connection, comprising a mounting plate configured to attach to a prosthetic limb socket of a user, an alignment mechanism configured to attach to the mounting plate, and a lower connector configured to attach to the alignment mechanism and to a prosthetic limb, wherein the alignment mechanism is configured to allow adjustment of the alignment of the lower connector with respect to the mounting plate with at least two degrees of freedom.

Particular embodiments may comprise one or more of the following features. The lower connector may have an upper surface configured to interface with the alignment mechanism and rotationally fix the lower connector with respect to the alignment mechanism. The lower connector may comprise a base and a main body and the bottom surface of the base may be configured to interface with the upper surface of the main body to rotationally fix the main body with respect to the base. Each of the bottom surface of the base and the upper surface of the main body may have a plurality of radial ridges and the pluralities of radial ridges on the bottom surface of the base and the upper surface of the main body may allow a rotational position of the main body with respect to the base to be adjusted. The alignment mechanism may comprise a base plate having a base plate aperture extending through the base plate, an outer cam configured to sit within the base plate aperture, wherein when the outer cam sits within the base plate aperture, a rotational position of the outer cam with respect to the base plate is fixed, the outer cam having an outer cam aperture extending through the outer cam offset from a center of the outer cam, and a center cam configured to sit within the outer cam aperture, wherein when the center cam sits within the outer cam aperture, a rotational position of the center cam with respect to the outer cam is fixed, the center cam having a center cam aperture offset from a center of the center cam. The base plate may be configured to attach to the mounting plate and hold the outer cam and the center cam against the mounting plate such that the center cam is maintained within the outer cam and the outer cam is maintained within the base plate. The outer cam may have an outer lip extending outward around a top outer edge of the outer cam and the outer lip may be configured to interlock with the base plate when the outer cam is positioned within the base plate to fix the rotational position of the outer cam with respect to the base plate. The center cam may have a center lip extending outward around a top outer edge of the center cam and the center lip may be configured to interlock with the outer cam when the center cam is positioned within the outer cam to fix the rotational position of the center cam with respect to the outer cam. The at least two degrees of freedom may be in a transverse plane and the prosthetic limb may be configured to be perpendicular to the transverse plane.

The foregoing and other aspects, features, and advantages will be apparent from the DESCRIPTION and DRAWINGS, and from the CLAIMS if any are included.

BRIEF DESCRIPTION OF THE DRAWINGS

Implementations will hereinafter be described in conjunction with the appended and/or included DRAWINGS, where like designations denote like elements, and:

FIG. 15 is a schematic illustrating potential positions for the center cam aperture;

FIG. 31 is a schematic illustrating potential positions of the adjustable prosthetic limb connection according to some implementations.

DETAILED DESCRIPTION

Figure 1:
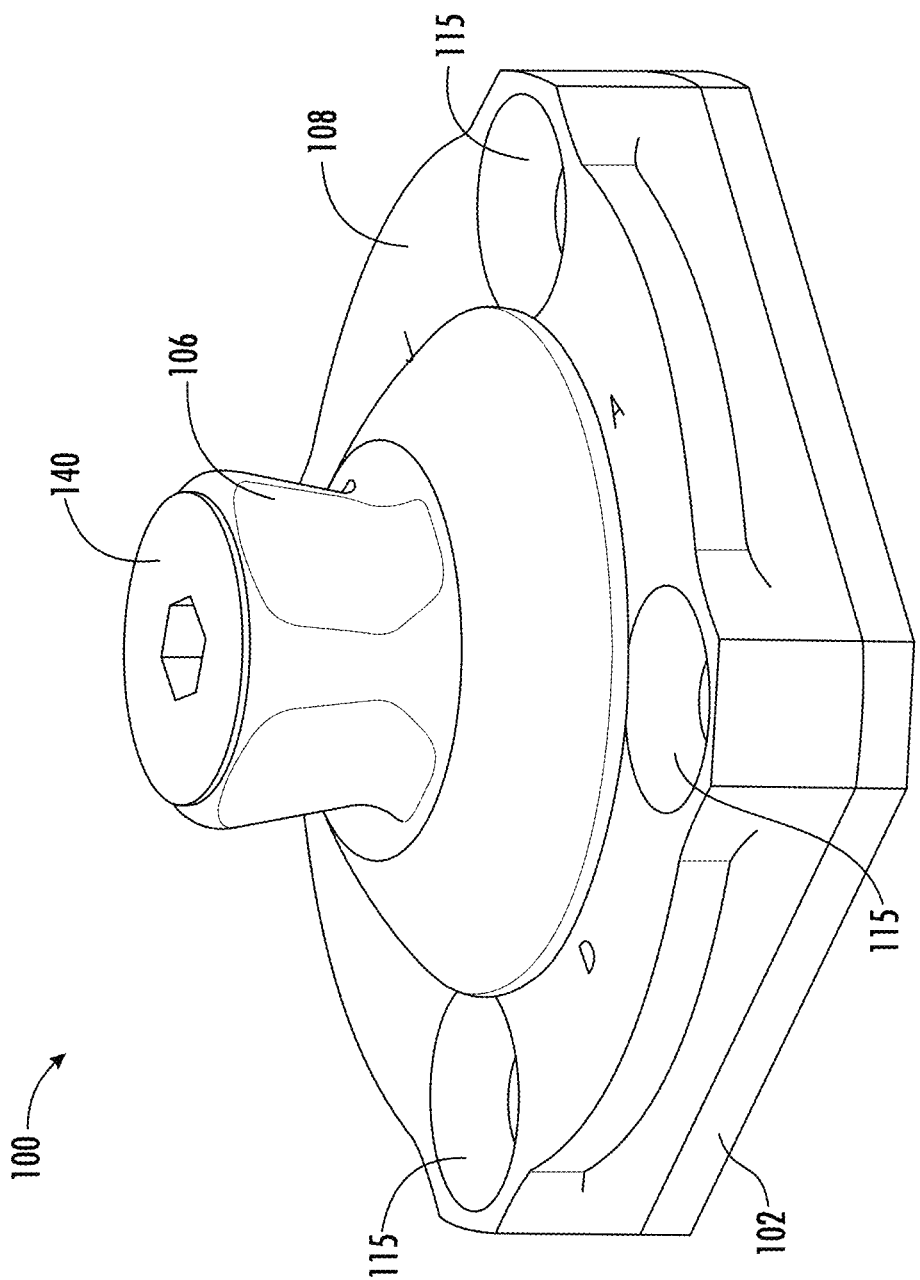
FIG. 1 is a perspective view of an adjustable prosthetic limb connection according to some implementations.
Figure 2:
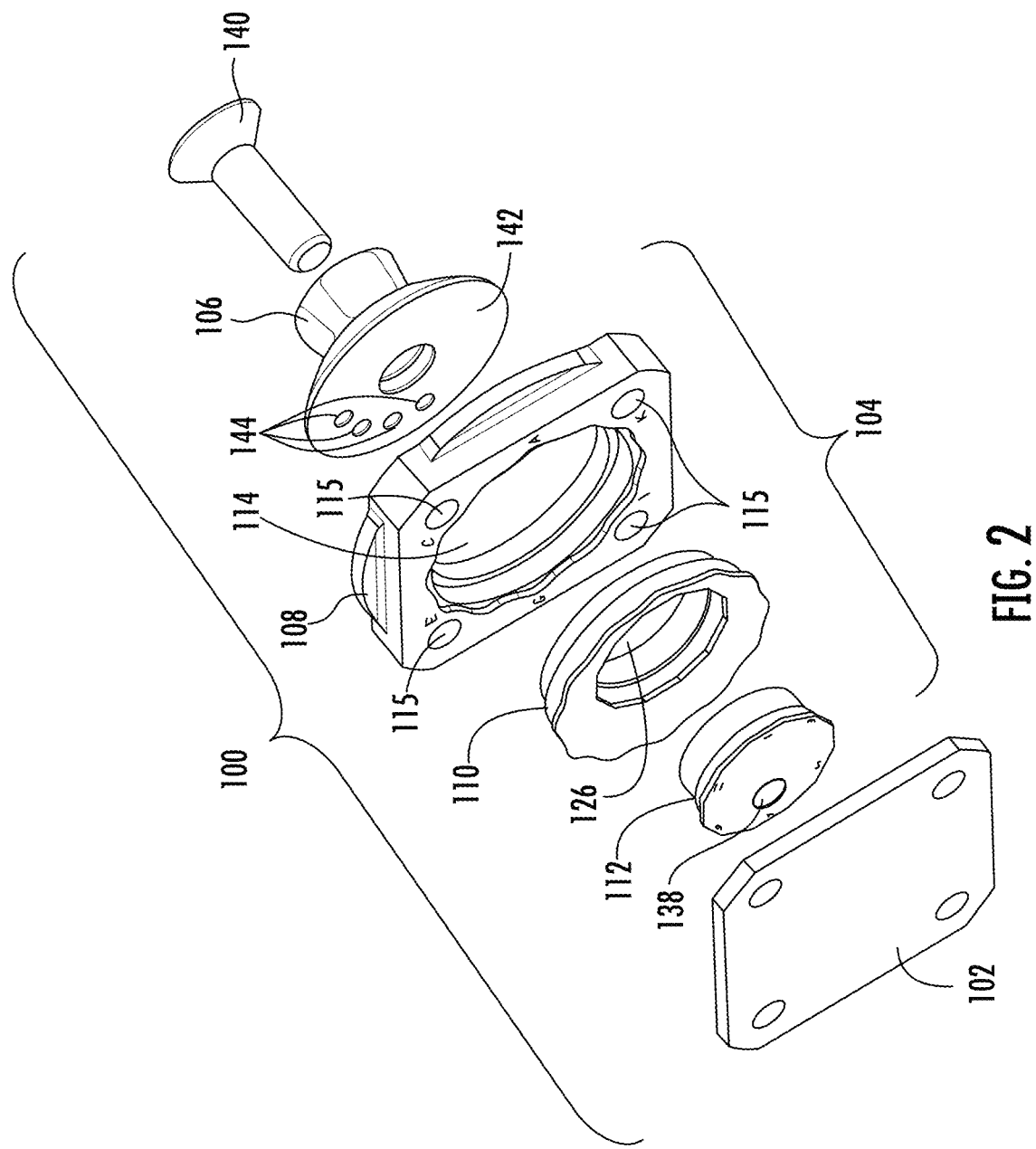
FIG. 2 is a top exploded view of an adjustable prosthetic limb connection according to some implementations.
Figure 3:
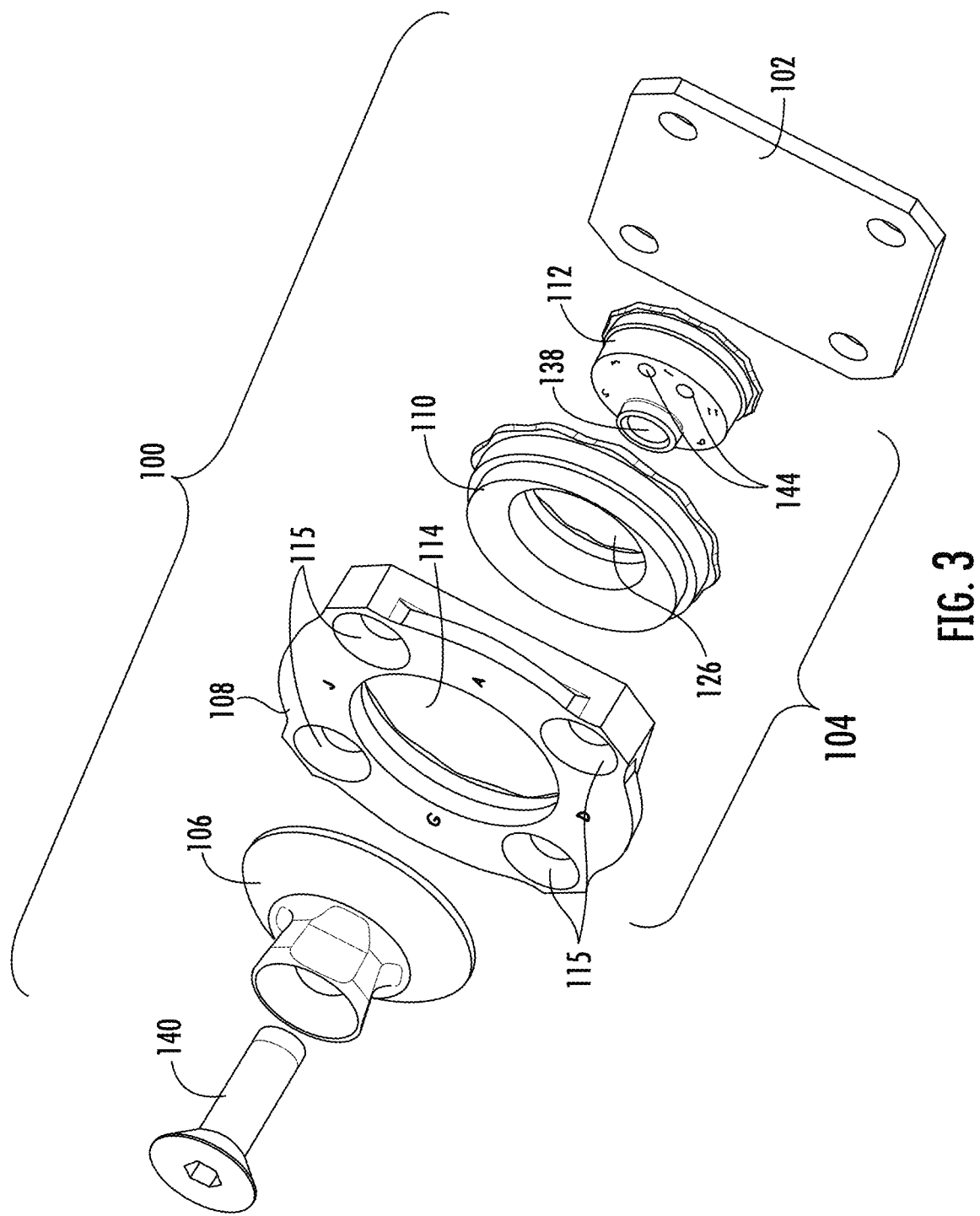
FIG. 3 is a bottom exploded view of an adjustable prosthetic limb connection according to some implementations.
Figure 4:
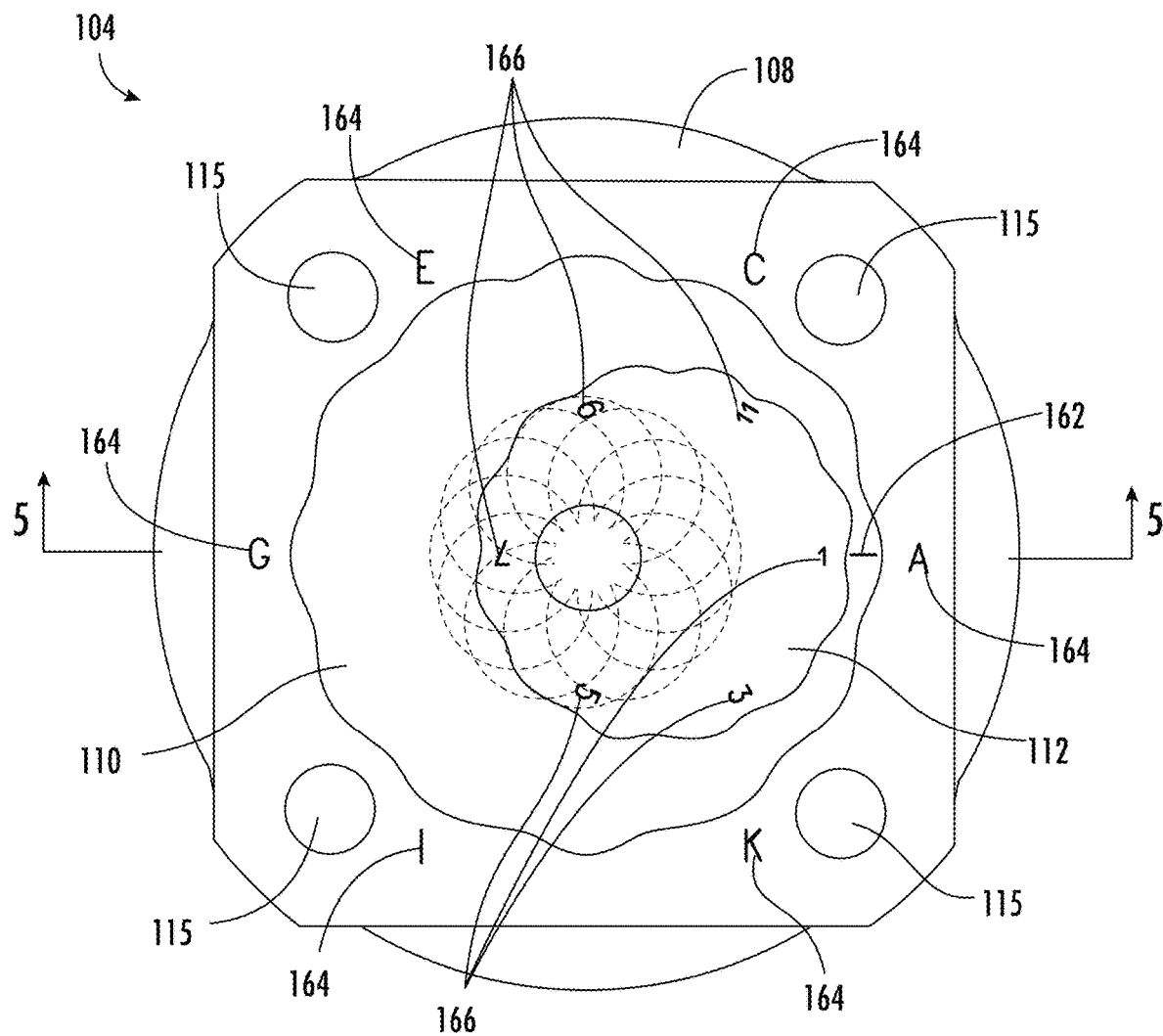
FIG. 4 is a top view of an adjustable prosthetic limb connection according to some implementations while in the A1 position.

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that implementations of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

When a range of values is expressed, another implementation includes from the one particular value and/or to the other particular value. Similarly, when values are expressed as approximations, by use of the antecedent "about," it will be understood that the particular value forms another embodiment. All ranges are inclusive and combinable.

Throughout the description and claims of this specification, the words "comprise" and "contain" and variations of the words, for example "comprising" and "comprises", mean "including but not limited to", and are not intended to (and do not) exclude other components.

As required, detailed embodiments of the present disclosure are included herein. It is to be understood that the disclosed embodiments and implementations are merely exemplary of the invention that may be embodied in various forms. Therefore, specific structural and functional details disclosed herein are not to be interpreted as limits, but merely as a basis for teaching one skilled in the art to employ the present invention. The specific examples below will enable the disclosure to be better understood. However, they are given merely by way of guidance and do not imply any limitation.

The present disclosure may be understood more readily by reference to the following detailed description taken in connection with the accompanying figures and examples, which form a part of this disclosure. It is to be understood that this disclosure is not limited to the specific materials, devices, methods, applications, conditions, or parameters described and/or shown herein, and that the terminology used herein is for the purpose of describing particular embodiments and implementations by way of example only and is not intended to be limiting of the claimed inventions. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

More specifically, this disclosure, its aspects and embodiments, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

For amputees, the socket into which the residual limb is inserted is typically custom made and completely unique to the amputee and the amputee's physiology. Because of that uniqueness, the line of force from the distal end of the socket to the ground does not necessarily line up with the center of the socket. Thus, adjustments have to be made to correctly place the line of force. Currently, to accomplish this, doctors typically start with multiple iterations using single direction adjustments to discover whether two directions of adjustment in the transverse plane are required to restore the amputee to previous levels of mobility and activity. However, to get the correct pressure on the weight bearing parts of the amputee's residual limb, the line of force frequently requires adjustment in two directions of the transverse plane at the same time.

After the iterations using single direction adjustments have determined that two directions of adjustment are needed, then adjustments are made in multiple directions. However, it frequently takes multiple iterations with an initial test socket, then at least one other iteration with a completely new test socket, which is followed by a new definitive socket. Thus, the process for fitting an amputee with a prosthetic is cumbersome, time-consuming, and has an increased cost due to multiple iterations.

The present disclosure is related to an adjustable prosthetic limb connection 100. The prosthetic limb connection 100 is designed to provide adjustability to the components of the prosthetic limb without significantly increasing the weight of the prosthetic limb so that an amputee can be fitted with a prosthetic limb and then use the same limb connection 100 through all iterations of the fitting process described above. This helps to decrease the cost by using the same connection and decreases the time needed for each fitting because the prosthetic limb connection 100 can be easily adjusted to new positions. The prosthetic limb connection 100 is easy to use and facilitates the prosthetic limb fitting process so that the line of force can be properly aligned based on the amputee's physiology. The prosthetic limb connection 100 is configured to be implemented with any known type of attachment to a prosthetic limb, including through suction, elevated vacuum, locking pin, or pin/suction.

In the overall system (not shown, but described for reference), there is a liner that fits securely on the residual limb of the amputee. That liner is in contact with the socket and may also be mechanically attached to the distal end of the socket with a pin. A silicone seal ring may sit between the liner and the socket to ensure there is also suction maintained inside the socket as air is evacuated through a one-way valve when the socket is donned. At the bottom of the socket, there is a pyramid connector that attaches to a pylon that attaches to the prosthetic foot. At the socket and foot end of that pylon, there are the sphere/pyramid connectors that allow for alignment adjustments. The presently disclosed prosthetic limb connection 100 is configured to either fit directly to the end of the socket and replace the current socket adapter, or in the case of pin and pin suction, attach to the existing pyramid/receiver fitting. The pylon and foot components then attach to the distal end of the prosthetic limb connection 100.

Figure 18:
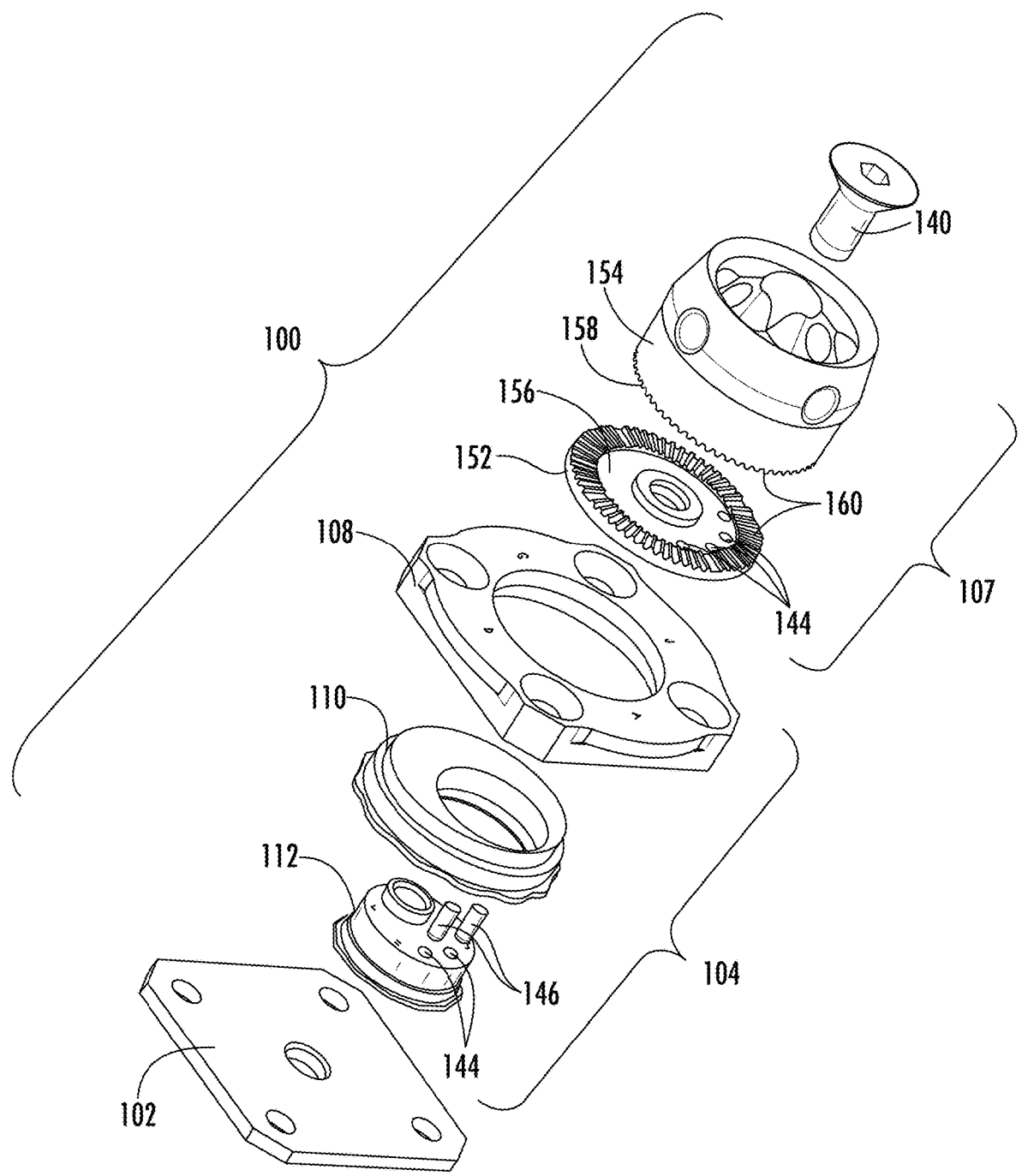
FIG. 18 is an exploded view of an adjustable prosthetic limb connection with an adjustable pyramid receiver mount according to some implementations.
Figure 19:
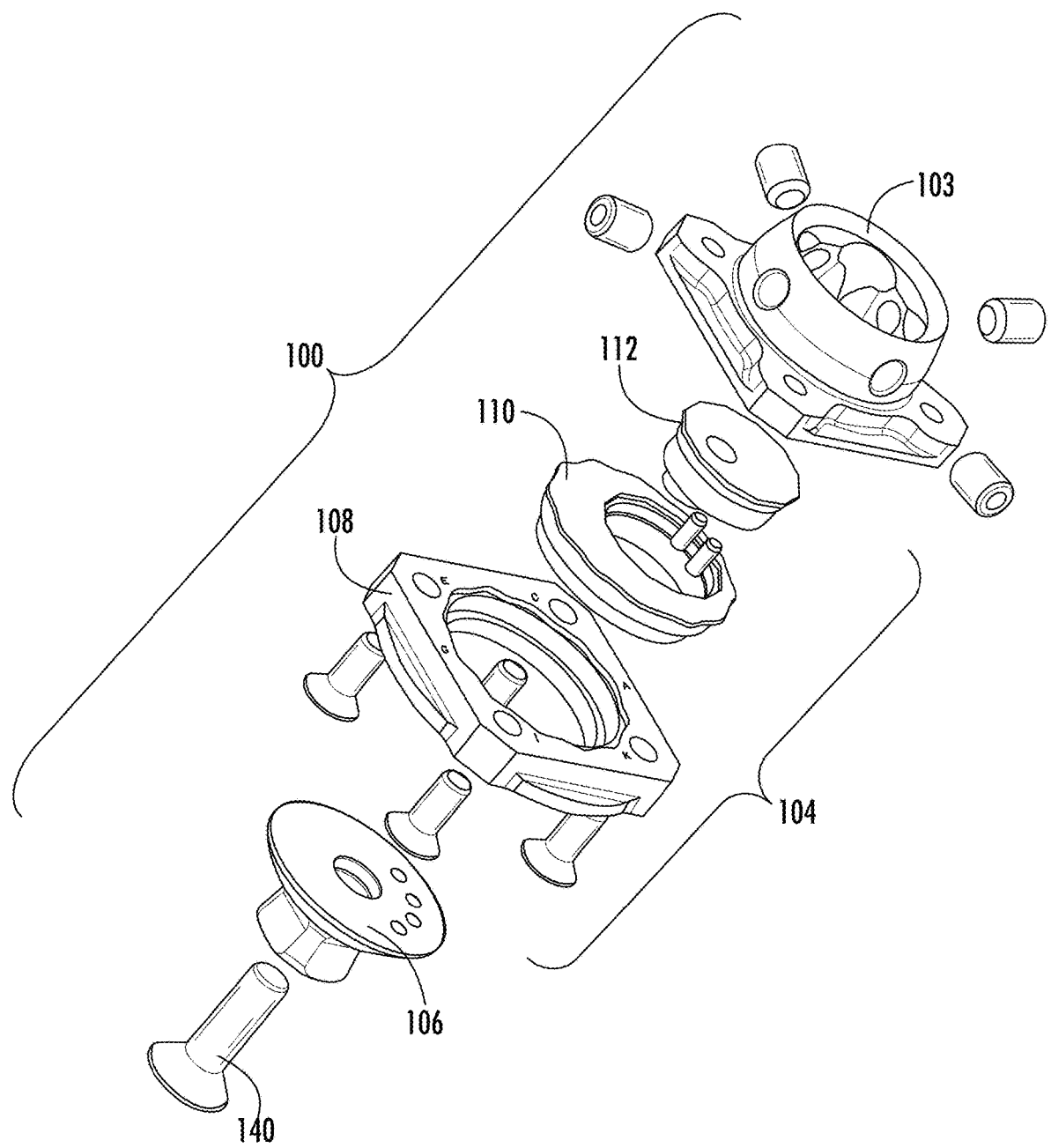
FIG. 19 is a top exploded view of an adjustable prosthetic limb connection with an adapter incorporated into the base plate for mounting to a pin or pin suction socket according to some implementations.
Figure 20:
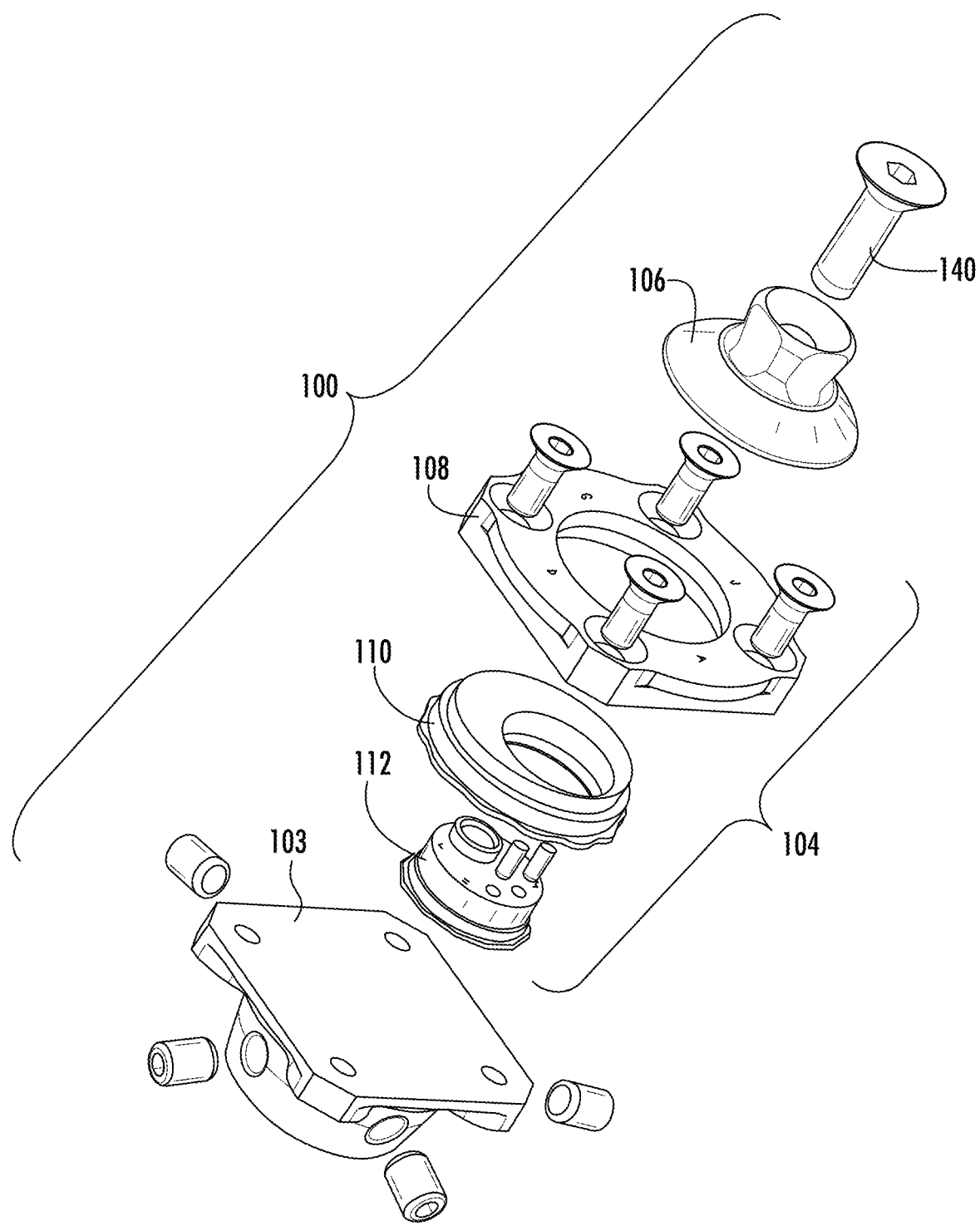
FIG. 20 is a bottom exploded view of an adjustable prosthetic limb connection with an adapter incorporated into the base plate for mounting to a pin or pin suction socket according to some implementations.

As shown in FIGS. 1-5, in some implementations, the prosthetic limb connection 100 comprises a mounting plate 102 configured to attach to a prosthetic limb socket of a user (not shown), an alignment mechanism 104 configured to attach to the mounting plate 102, and/or a lower connector 106 configured to attach to the alignment mechanism 104. In implementations designed for use with a pin-suction mount, the mounting plate 102 may be replaced with mounting plate 103 to allow the prosthetic limb connection 100 to mount to the pin (see FIGS. 19 and 20). The mounting plate 103 may include a pyramid receiver to mount to the pin and allow the prosthetic limb connection 100 to securely attach to the socket. In some implementations, the mounting plate 103 has threaded holes to allow screws to extend through the screw holes 115 of the base plate 108 and attach to the mounting plate 103. This may be different from the mounting plate 102, which may have unthreaded holes that allow the screws to pass through to attach to the socket of the user. The lower connector 106 is also configured to attach to a prosthetic limb (not shown). The lower connector 106 has a pyramid configuration. In some implementations, the lower connector 106 may be replaced with lower connector 107 which has a pyramid receiver configuration (FIG. 18). Though the majority of this disclosure discusses the lower connector 106, it is contemplated that the lower connector 107 may have any of the same features as the lower connector 106 and may be used in the same way. The prosthetic limb connection 100 connects the prosthetic limb to the prosthetic limb socket through the lower connector 106, the alignment mechanism 104, and the mounting plate 102. Generally, proper alignment of the line of force discussed above involves making the center axis of the lower connector 106 colinear with the line of force. For this reason, adjustment in two different dimensions is frequently required.

The alignment mechanism 104 is configured to allow adjustment of the alignment of the lower connector 106 with respect to the mounting plate 102. This is what allows the line of force through the prosthetic limb to be properly aligned to fit the amputee's unique physiology. The alignment mechanism 104 is configured to allow adjustment of the alignment of the lower connector 106 with respect to the mounting plate 102 with at least two degrees of freedom. Depending on the implementation, these two degrees of freedom may both be created by an adjustment of angular position, may both be created by an adjustment of linear position, or may be created by one adjustment of angular position and one adjustment of linear position. In some implementations, each of the degrees of freedom occur in a transverse plane where the prosthetic limb is configured to be perpendicular to the transverse plane. In this way, the alignment mechanism 104 is configured to adjust the alignment of the lower connector 106 with respect to the mounting plate 102 in the transverse plane without adjusting an orientation of the axis of the prosthetic limb or moving the prosthetic limb in a direction perpendicular to the transverse plane. However, in some implementations, the prosthetic limb connection 100 may also be configured to provide additional degrees of freedom outside of the transverse plane.

Figure 6:
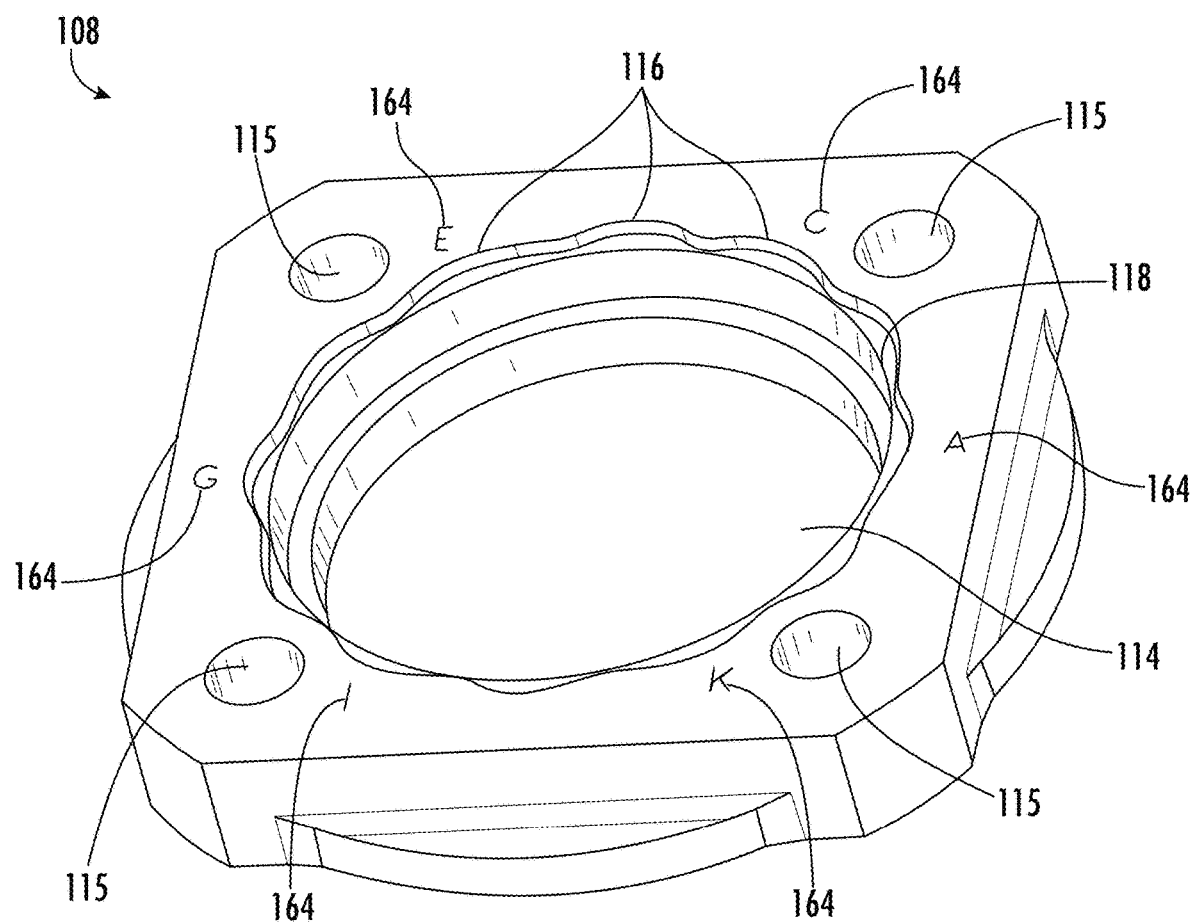
FIG. 6 is a top perspective view of a base plate of an adjustable prosthetic limb connection according to some implementations.
Figure 7:
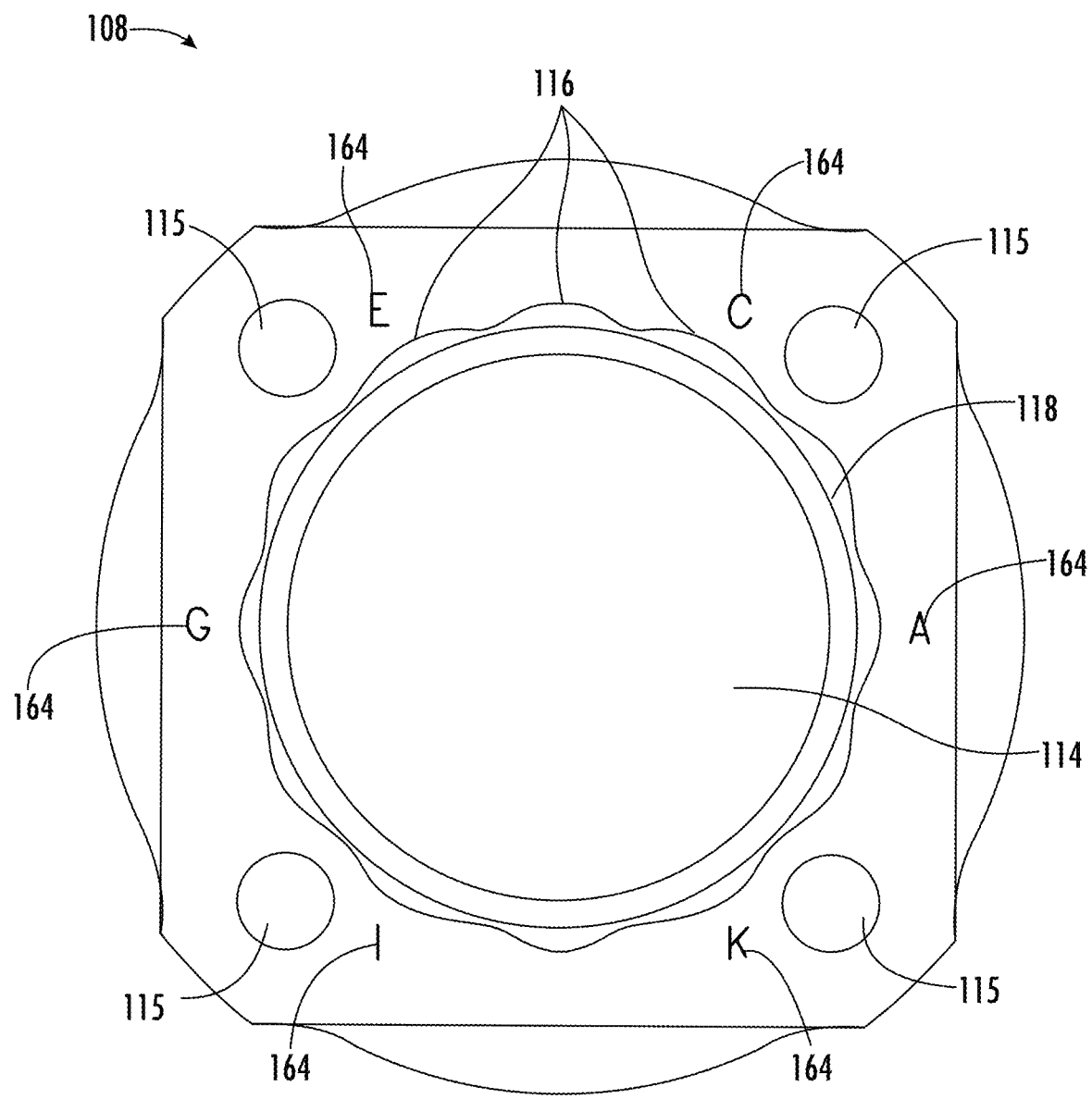
FIG. 7 is a top view of a base plate of an adjustable prosthetic limb connection according to some implementations.
Figure 8:
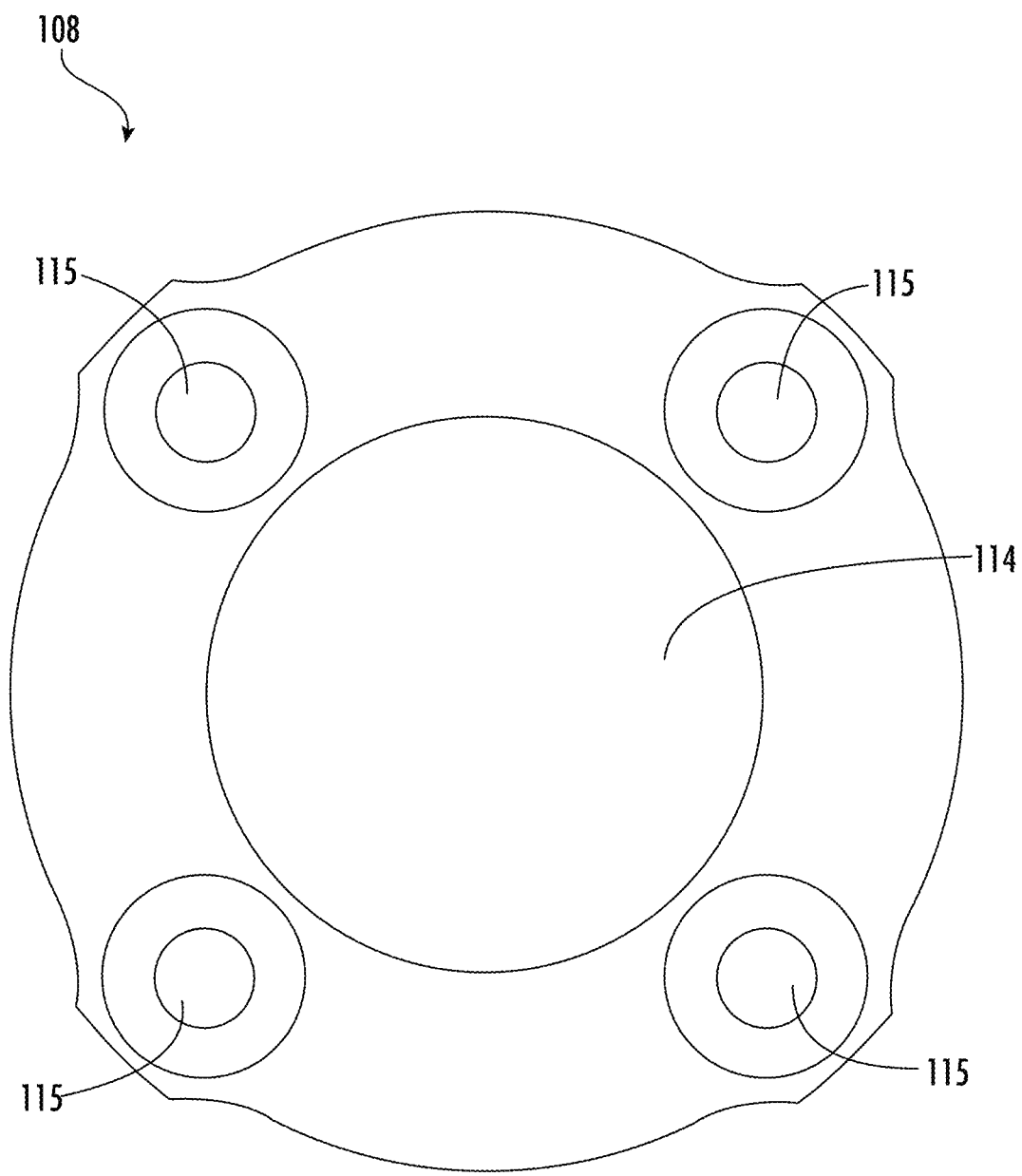
FIG. 8 is a bottom view of a base plate of an adjustable prosthetic limb connection according to some implementations.

In some implementations, the alignment mechanism 104 comprises a base plate 108, an outer cam 110, and/or a center cam 112. As shown in FIGS. 6-8, the base plate 108 has a base plate aperture 114 and a plurality of screw holes 115 extending through the base plate 108. The base plate 108 may also have a plurality of grooves 116 extending outward around a top inner edge 118 of the base plate 108. The top inner edge 118 of the base plate 108 is the edge created by the base plate aperture 114 and the plurality of grooves 116 extend outward from the base plate aperture 114 into the base plate 108. The plurality of grooves 116 may form a wave pattern as shown or may have any other shape.

Additionally, the plurality of grooves 116 may be spaced apart by a regular interval around the periphery of the base plate aperture 114.

As discussed in more detail below, in some implementations, the outer cam 110 is configured to nest or be positioned within the base plate 108 and the center cam 112 is configured to nest or be positioned within the center cam 112. In some implementations, the base plate 108 is configured to hold the outer cam 110 and the center cam 112 against the mounting plate 102 such that, absent intervention by a user, the center cam 112 is maintained within the outer cam 110 and the outer cam 110 is maintained within the base plate 108. Screws may extend through the screw holes 115 of the base plate 108 and through the mounting plate 102 to hold the outer cam 110 and the center cam 112 against the mounting plate 102.

Figure 9:
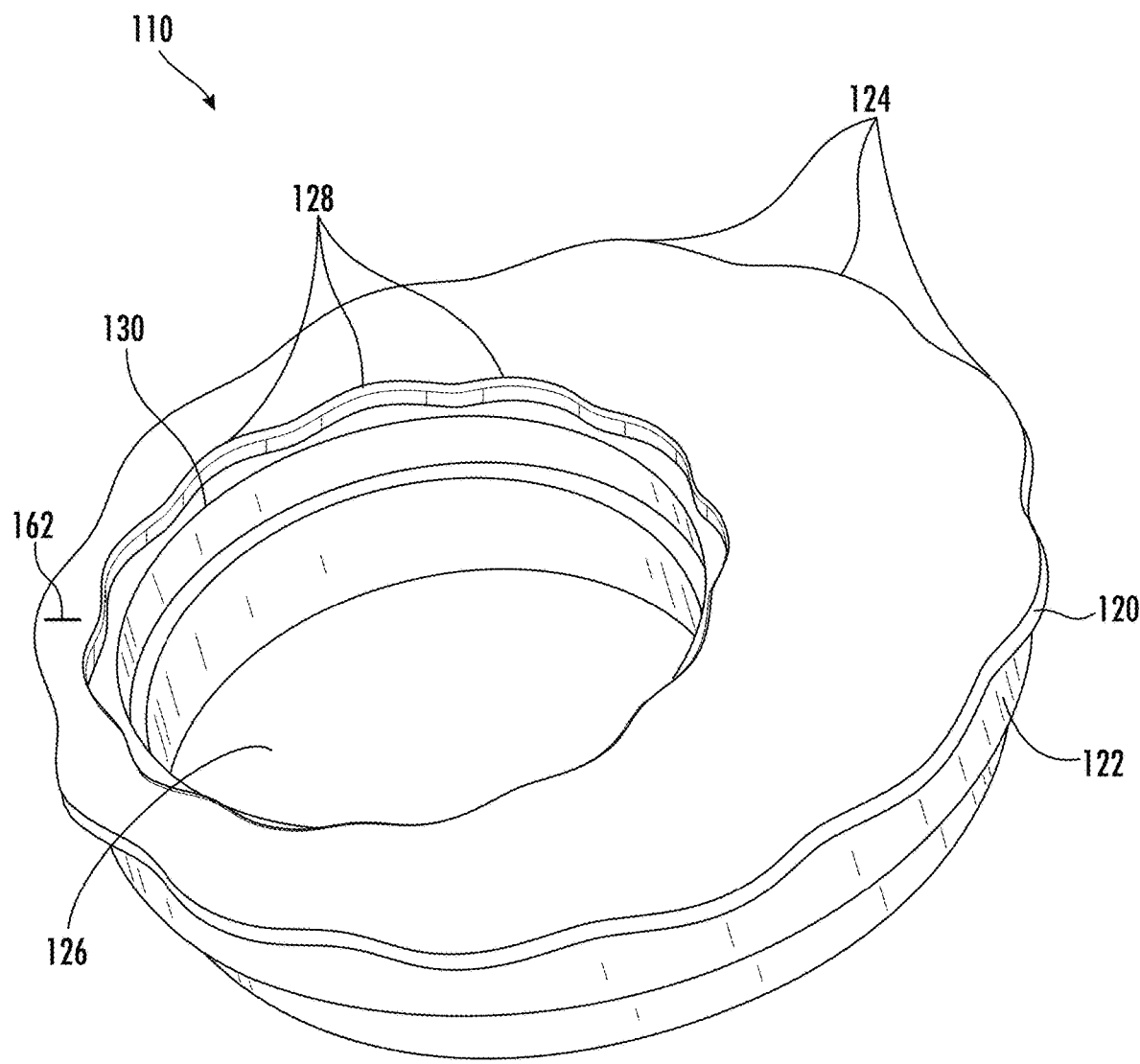
FIG. 9 is a top perspective view of an outer cam of an adjustable prosthetic limb connection according to some implementations.
Figure 10:
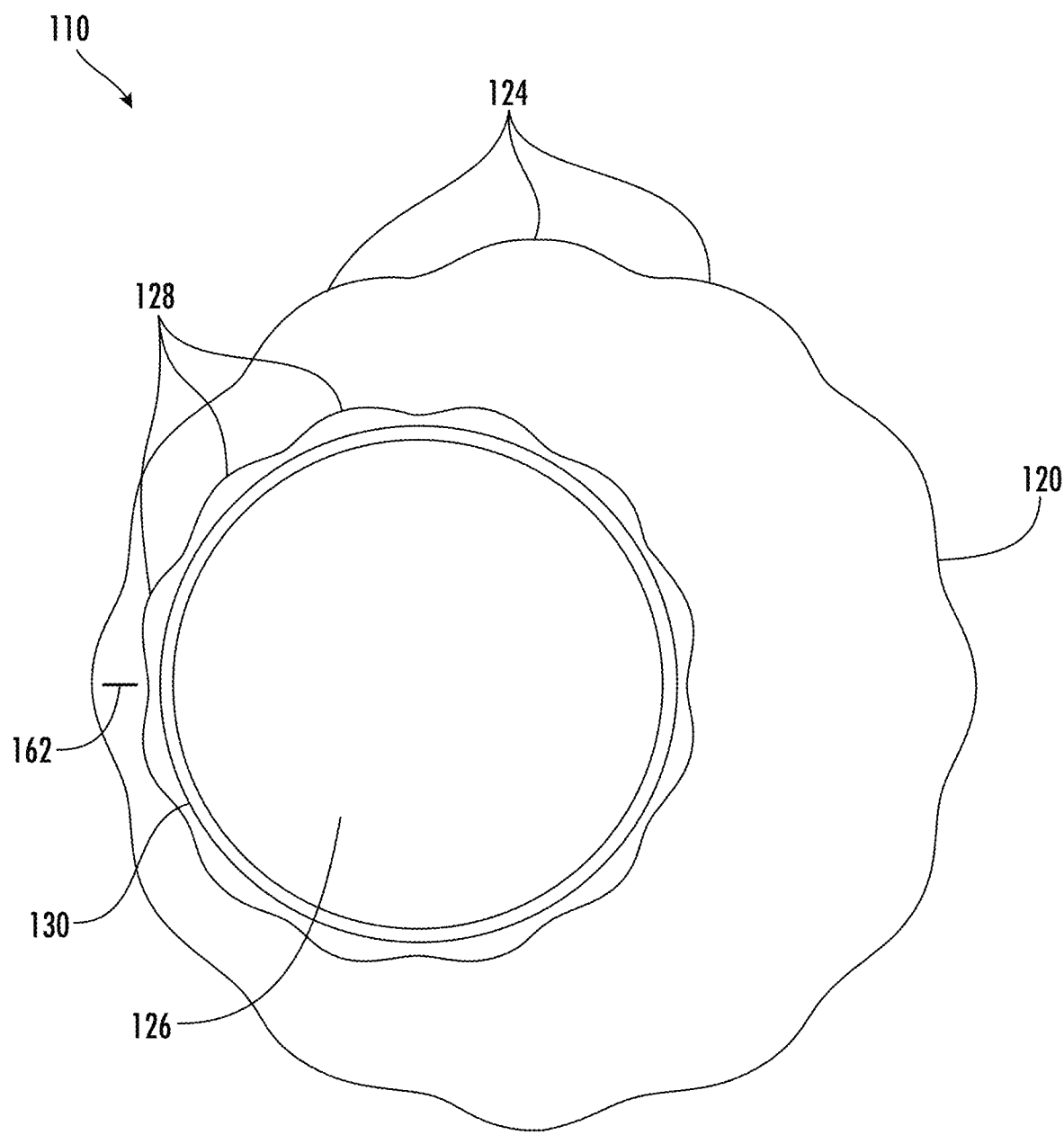
FIG. 10 is a top view of an outer cam of an adjustable prosthetic limb connection according to some implementations.
Figure 11:
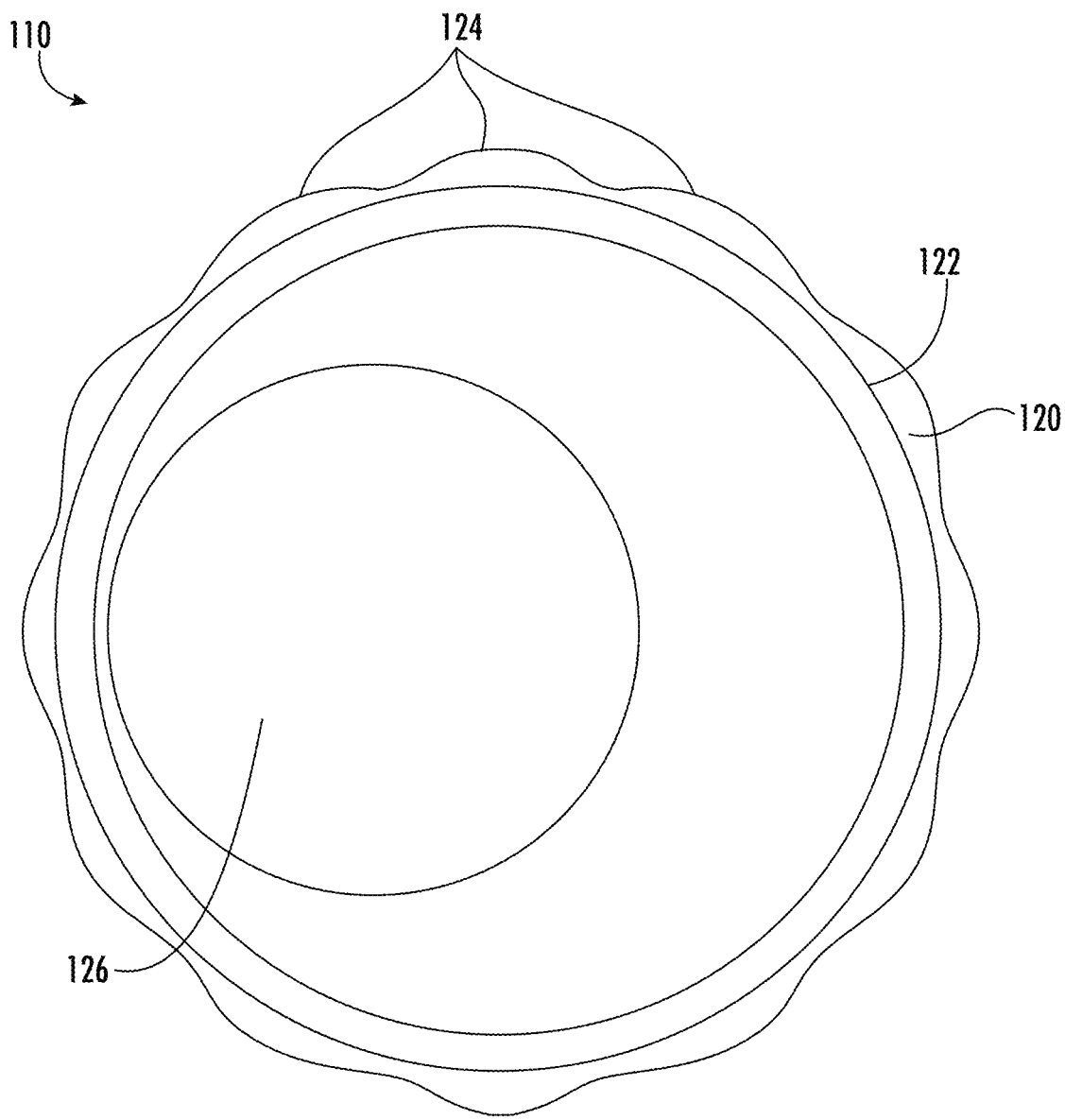
FIG. 11 is a bottom view of an outer cam of an adjustable prosthetic limb connection according to some implementations.

The outer cam 110 is configured to sit within the base plate aperture 114 of the base plate 108. As shown in FIGS. 9-11, the outer cam 110 has an outer lip 120 extending outward around a top outer edge 122 of the outer cam 110. This outer lip 120 has a plurality of ridges 124 positioned around the top outer edge 122 of the outer cam 110. The plurality of ridges 124 are configured to interlock with the plurality of grooves 116 of the base plate 108 when the outer cam 110 is positioned within the base plate 108. This helps to fix a rotational position of the outer cam 110 with respect to the base plate 108 when the outer cam 110 sits within the base plate aperture 114 of the base plate 108. In some implementations, the plurality of ridges 124 is shaped to conform to the plurality of grooves 116.

In some implementations, the outer cam 110 has an outer cam aperture 126 extending through the outer cam 110. When the outer cam 110 sits within the base plate aperture 114, in some implementations, the outer cam aperture 126 is parallel with the base plate aperture 114. However, in some implementations, a center axis of the outer cam aperture 126 is noncolinear and/or nonconcentric with a center axis of the base plate aperture 114 and the outer cam aperture 126 is offset from a center of the outer cam 110. Similar to the base plate 108, the outer cam 110 also may have a plurality of grooves 128 extending outward around a top inner edge 130 of the outer cam 110 surrounding the outer cam aperture 126. The top inner edge 130 of the outer cam 110 is the edge created by the outer cam aperture 126 and the plurality of grooves 128 extend outward from the outer cam aperture 126 into the outer cam 110. The plurality of grooves 128 may form a wave pattern as shown or may have any other shape. Additionally, the plurality of grooves 128 may be spaced apart by a regular interval around the periphery of the outer cam aperture 126.

Figure 12:
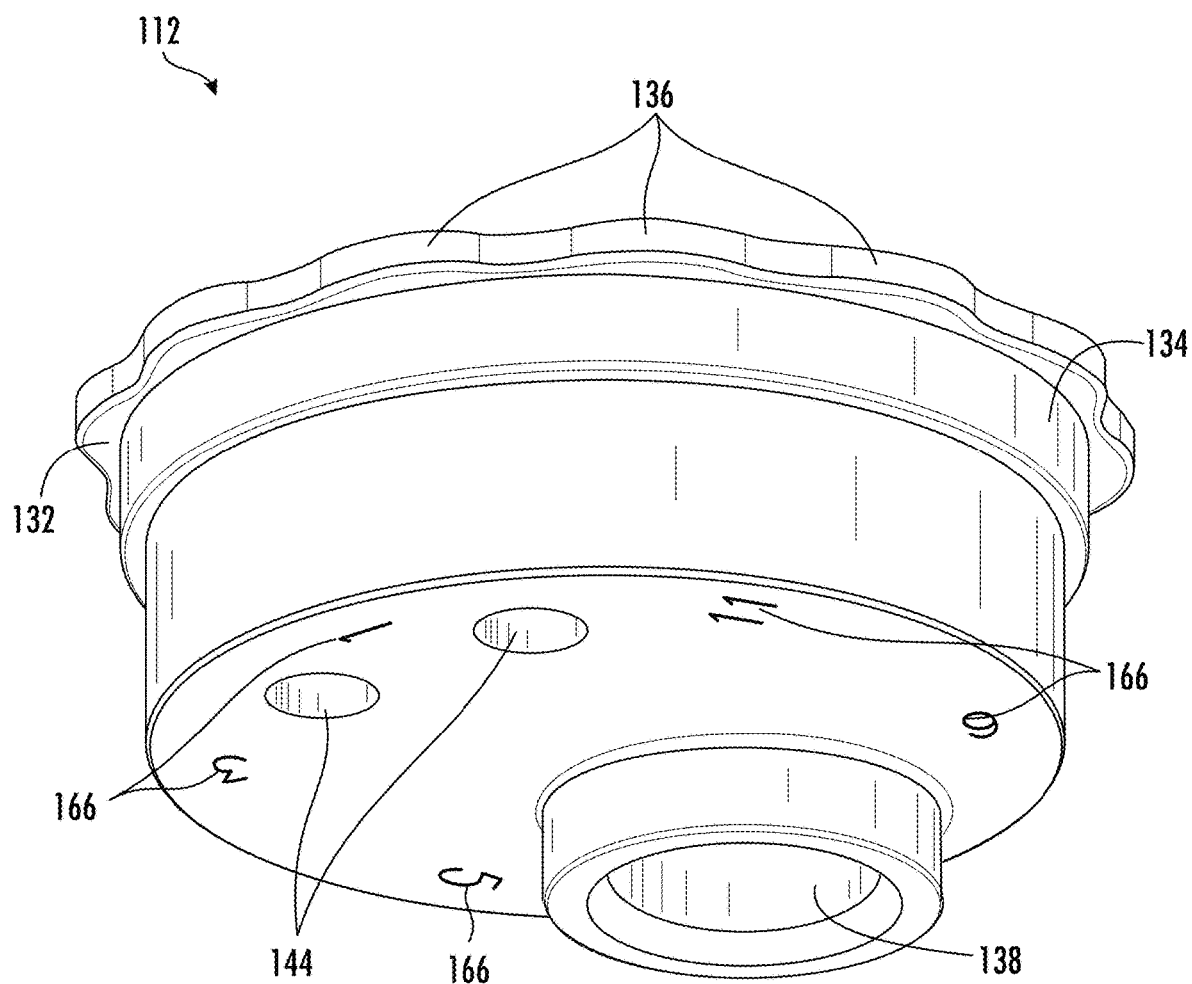
FIG. 12 is bottom perspective view of a center cam of an adjustable prosthetic limb connection according to some implementations.
Figure 13:
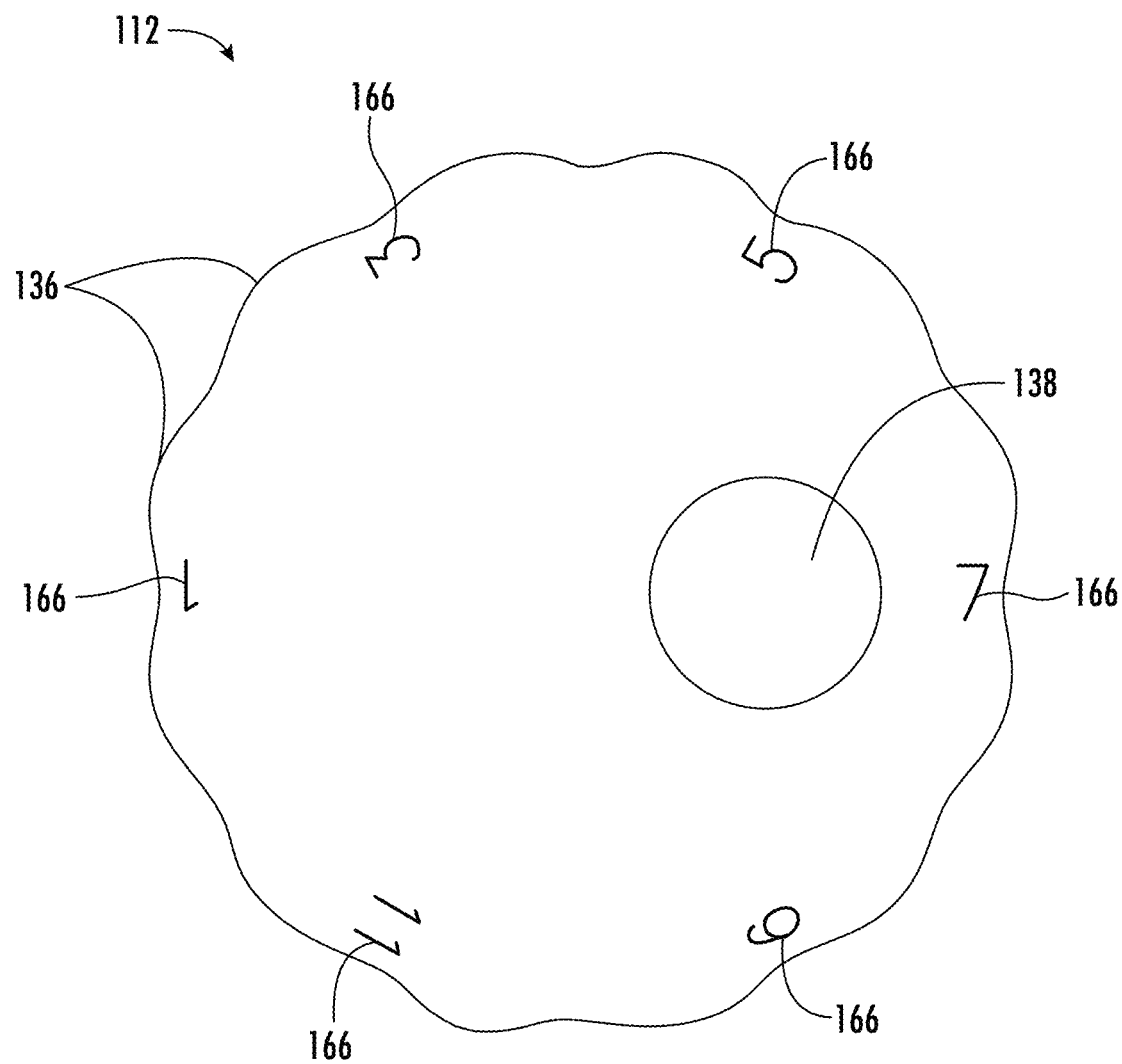
FIG. 13 is a top view of a center cam of an adjustable prosthetic limb connection according to some implementations.
Figure 14:
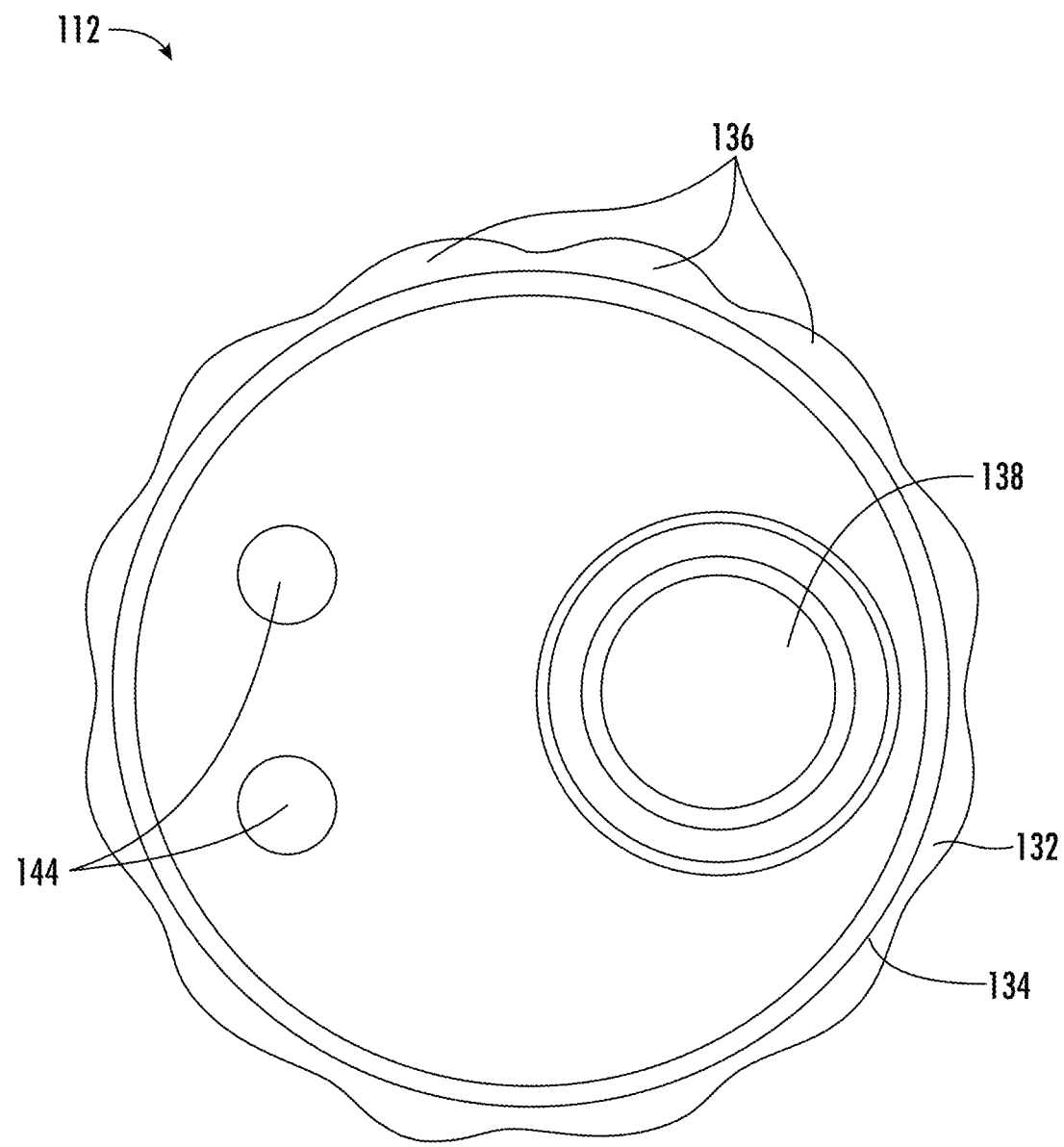
FIG. 14 is a bottom view of a center cam of an adjustable prosthetic limb connection according to some implementations.

The center cam 112 is configured to sit within the outer cam aperture 126 of the outer cam 110. As shown in FIGS. 12-14, the center cam 112 has a center lip 132 extending outward around a top outer edge 134 of the center cam 112. Like the outer lip 120 of the outer cam 110, the center lip 132 has a plurality of ridges 136 positioned around the top outer edge 134 of the center cam 112. The plurality of ridges 136 are configured to interlock with the plurality of grooves 128 of the outer cam 110 when the center cam 112 is positioned within the outer cam 110. This helps to fix a rotational position of the center cam 112 with respect to the outer cam 110 when the center cam 112 sits within the outer cam aperture 126 of the outer cam 110. In some implementations, the plurality of ridges 136 is shaped to conform to the plurality of grooves 128.

Figure 5:
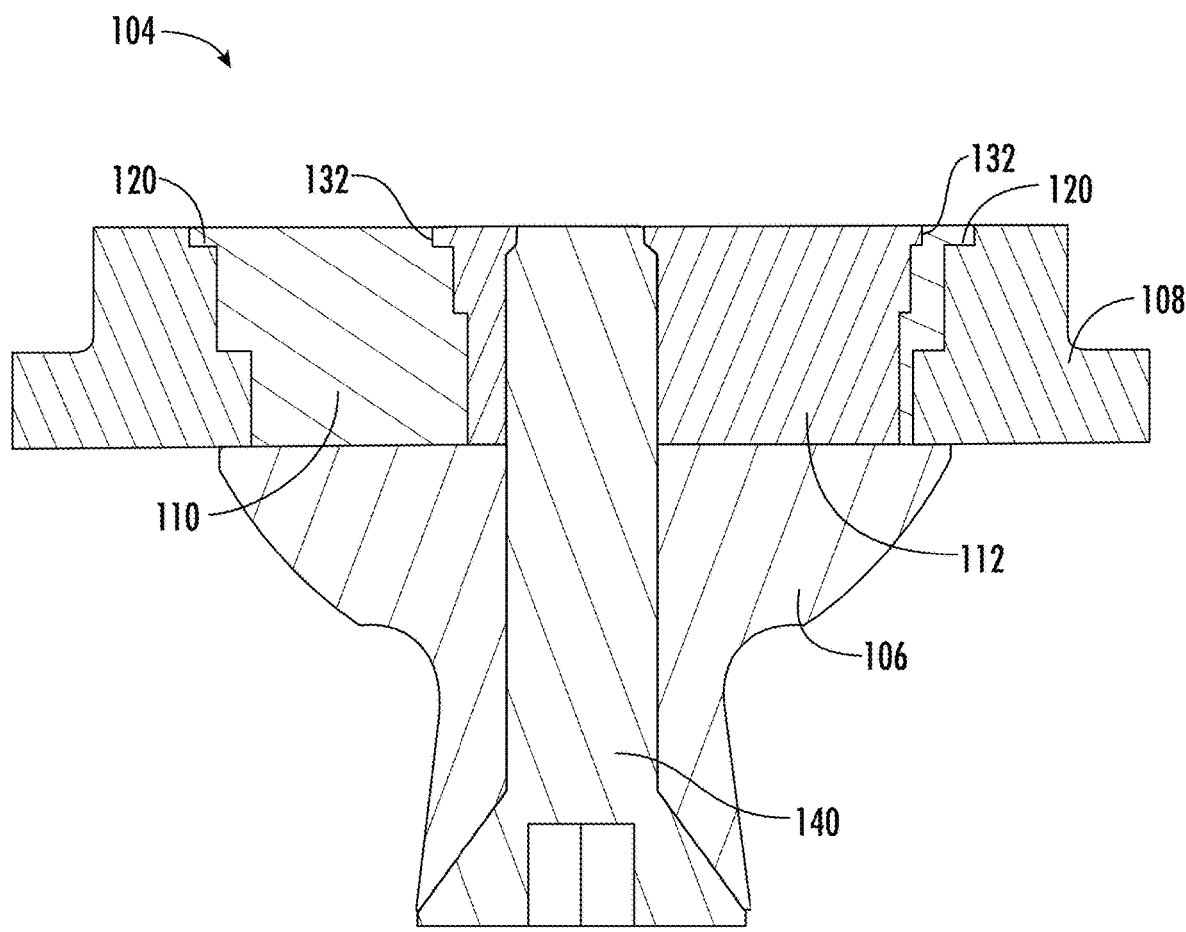
FIG. 5 is a cross section of an adjustable prosthetic limb connection according to some implementations taken along line 5-5 in FIG. 4.

In some implementations, like the outer cam 110, the center cam 112 has a center cam aperture 138 extending through the center cam 112. When the center cam 112 sits within the outer cam aperture 126, in some implementations, the center cam aperture 138 is parallel with the outer cam aperture 126. However, in some implementations, a center axis of the center cam aperture 138 is noncolinear and/or nonconcentric with the center axis of the outer cam aperture 126 and the center cam aperture 138 is offset from a center of the center cam 112. In some implementations, the lower connector 106 is configured to align with the center cam aperture 138. The prosthetic limb connection 100 may comprise a fastener 140 that is configured to extend through the lower connector 106 and couple with the center cam aperture 138 of the center cam 112, as shown in FIG. 5. This couples the lower connector 106 with the center cam 112. In some implementations, the center cam aperture 138 is threaded and the fastener 140 is configured to mechanically couple with the center cam aperture 138 with a thread or in any other manner.

In some implementations, the outer cam 110 is circular, with the exception of the outer lip 120. This allows the outer cam 110 to rotate within the base plate aperture 114, as long as the plurality of ridges 124 has not interlocked with the plurality of grooves 116 as described above. This allows the alignment mechanism 104 to be adjusted without requiring that the outer cam 110 be completely removed from the base plate 108. Instead, the outer cam 110 can be rotated once the outer cam 110 is only slightly removed from the base plate aperture 114. Once the outer cam 110 has been rotated to the desired position, the outer cam 110 can be inserted completely into the base plate aperture 114 so that the plurality of ridges 124 interlocks with the plurality of grooves 116, thus locking the rotational position of the outer cam 110 with respect to the base plate 108. The number of ridges 124 included in the plurality of ridges 124 and the number of grooves 116 included in the plurality of grooves 116 determines the number of discrete points at which the rotation of the outer cam 110 can be locked with respect to the base plate 108.

Similarly, in some implementations, the center cam 112 is circular, with the exception of the center lip 132. This allows the center cam 112 to rotate within the outer cam aperture 126, as long as the plurality of ridges 136 has not interlocked with the plurality of grooves 128 as described above. This allows the alignment mechanism 104 to be adjusted without requiring that the center cam 112 be completely removed from the outer cam 110. Instead, the center cam 112 can be rotated once the center cam 112 is only slightly removed from the outer cam aperture 126. Once the center cam 112 has been rotated to the desired position, the center cam 112 can be inserted completely into the outer cam aperture 126 so that the plurality of ridges 136 interlocks with the plurality of grooves 128, thus locking the rotational position of the center cam 112 with respect to the outer cam 110. The number of ridges 136 included in the plurality of ridges 136 and the number of grooves 128 included in the plurality of grooves 128 determines the number of discrete points at which the rotation of the center cam 112 can be locked with respect to the outer cam 110.

In some implementations, because the outer cam aperture 126 is offset from the center of the outer cam 110, when the outer cam 110 is rotated to a new position within the base plate aperture 114, the outer cam aperture 126 is moved to a new position with respect to the base plate 108. This also moves the center cam 112 to a new position with respect to the base plate 108. Similarly, in some implementations, because the center cam aperture 138 is offset from the center of the center cam 112, when the center cam 112 is rotated to a new position within the outer cam aperture 126, the center cam aperture 138 is moved to a new position with respect to the outer cam 110. This also moves the lower connector 106 to a new position with respect to the outer cam 112. In such implementations, these two rotations thus provide two degrees of freedom in adjusting the position of the lower connector 106 with respect to the mounting plate 102.

Therefore, the alignment mechanism 104 can be adjusted by loosening the alignment mechanism 104 to allow the center cam 112 to be lifted out of the outer cam 110 and/or the outer cam 110 to be lifted out of the base plate 108. The center cam 112 and/or the outer cam 110 can then be rotated to a new desired position and the alignment mechanism 104 can be tightened to lock the rotational position of the center cam 112 and the outer cam 110. In this way, the alignment of the lower connector 106 with respect to the mounting plate 102 can be adjusted, and therefore the alignment of the line of force can be adjusted to properly place the line of force and allow the amputee to return to previous levels of mobility and activity. The simplicity of this adjustment is a significant improvement over the current process of repeatedly refitting the amputee with new sockets each time an adjustment is required. Using the prosthetic limb connection 100 disclosed herein, a prosthetist can adjust the prosthetic limb to a new position in just a few minutes.

In addition to being simple, the alignment mechanism 104 described above also provides a large number of unique positions where the lower connector 106 can be fixed with respect to the mounting plate 102. The number of unique positions is dependent on the number of ridges 124 on the outer cam 110 and grooves 116 on the base plate 108, as well the number of ridges 136 on the center cam 112 and grooves 128 on the outer cam 110. In some implementations, there are twelve ridges 124, twelve grooves 116, twelve ridges 136, and twelve grooves 128. This allows for twelve discrete positions of the outer cam 110 within the base plate 108 at 30-degree increments, and twelve discrete position of the center cam 112 within the outer cam 110 at 30-degree increments. In such implementations, there are a total of 73 unique positions for the lower connector 106 to be fixed with respect to the mounting plate 102. Any number of each of the components may be implemented. In some implementations, the number of ridges 124 matches the number of grooves 116 and the number of ridges 136 matches the number of grooves 128.

Figure 15:
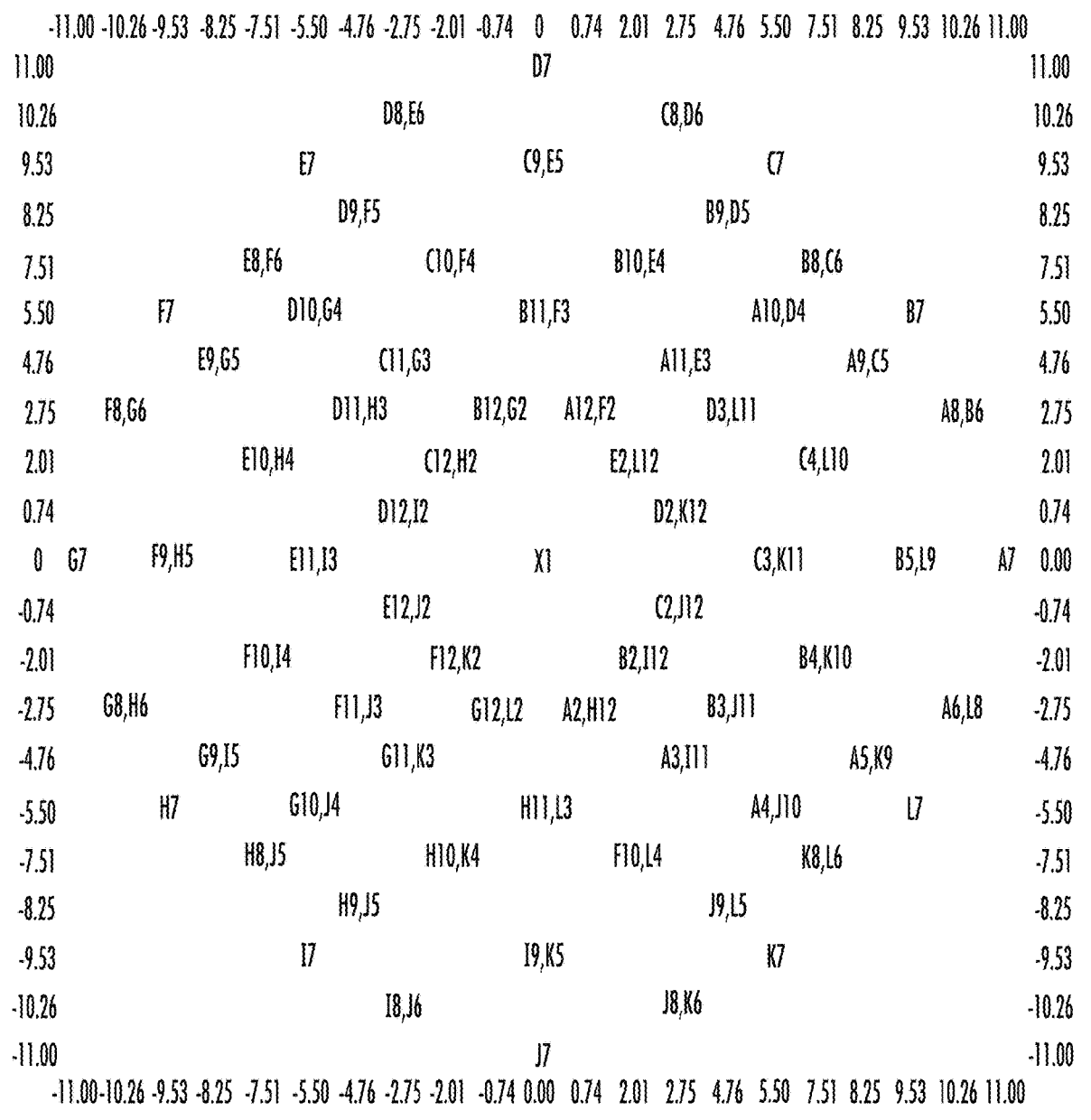
Figure 16:
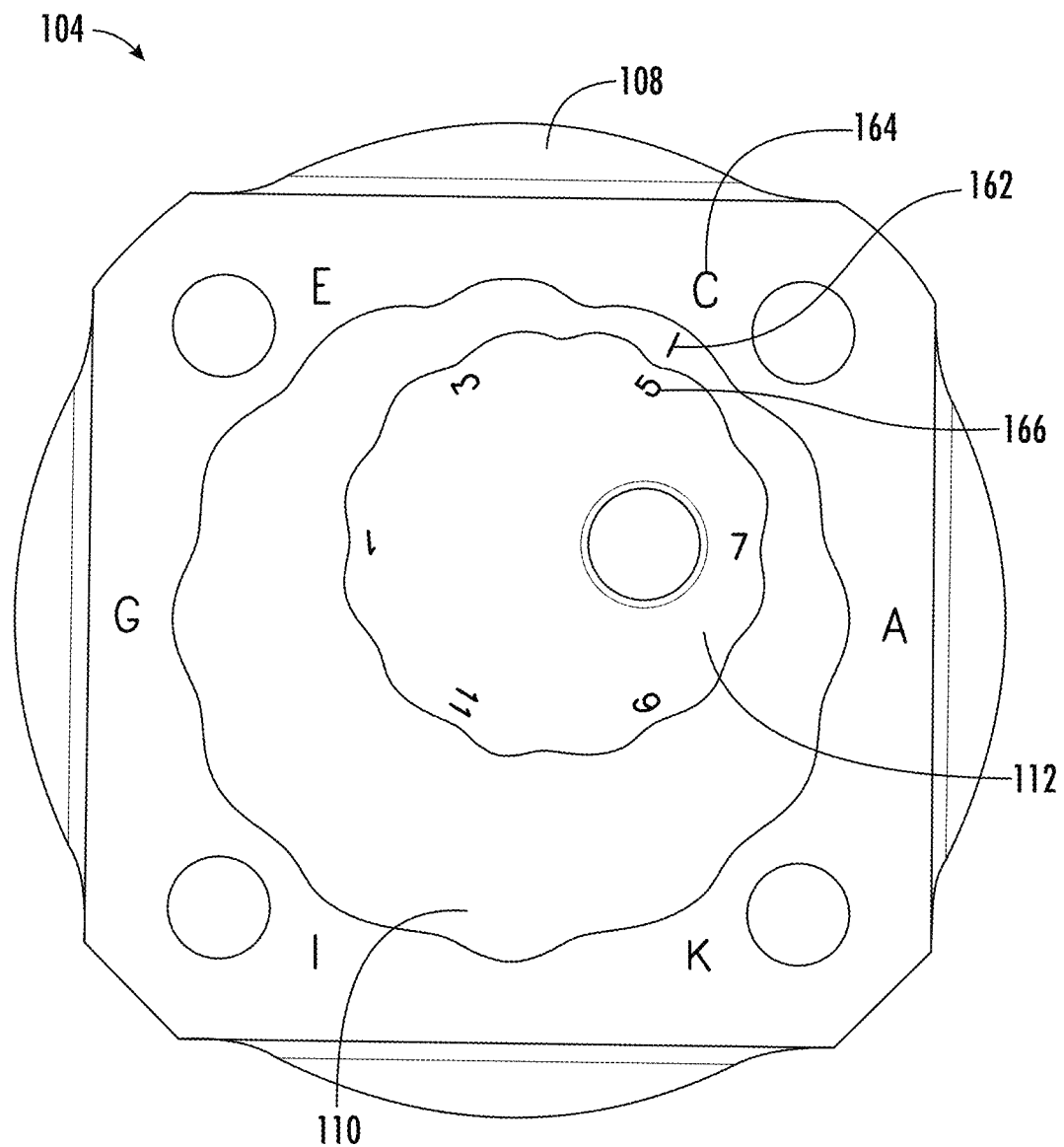
FIG. 16 is a top view of an adjustable prosthetic limb connection according to some implementations while in the C5 position.

The outer cam 110 may comprise a position marker 162 aligned with a particular ridge 124 of the plurality of ridges 124, which may also be aligned such that a line can be drawn from the center of the outer cam 110 through the center of the outer cam aperture 126, through the position marker 162, and through the particular ridge 124. In some implementations, the position marker 162 is also aligned halfway between two grooves 128 of the plurality of grooves 128. In addition, in some implementations, position labels 164 may be assigned to each of the plurality of grooves 116 of the base plate 108, though some position labels 164 may be skipped. For example, position labels 164 may only be physically written adjacent to every other groove 116, as shown. Similarly, in some implementations, position labels 166 may be assigned to halfway between each of the plurality of ridges 136 of the center cam 112, though some position labels 166 may be skipped. For example, position labels 166 may only be physically written halfway between each of the plurality of ridges 136, as shown. This allows the position marker 162 to be aligned with a position label 164 and a position label 166 in each fixed position of the outer cam 110 and the center cam 112 so that the current position can always be completely identified. Each possible position for a prosthetic limb connection 100 with twelve ridges 124, twelve grooves 116, twelve ridges 136, and twelve grooves 128 is depicted in the chart in FIG. 15. As shown, some positions have multiple labels due to overlap. FIG. 16 illustrates one example of a prosthetic limb connection 100 in the C5 position. The position marker 162 and position labels 164 and 166 thus allow a user who desires to adjust the alignment mechanism 104 to know exactly which positions have previously been tried and what other positions are available.

In some implementations, the lower connector 106 has an upper surface 142 that is configured to interface with the center cam 112 and rotationally fix the lower connector 106 with respect to the center cam 112. The upper surface 142 may provide clocking for the prosthetic limb to ensure proper alignment. This allows the lower connector 106, after being positionally adjusted using the alignment mechanism 104 to properly align the line of force through the prosthetic limb, to also be rotationally adjusted to orient the prosthetic limb in the appropriate direction. The lower connector 106 may interface with the center cam 112 in a variety of ways. For example, the lower connector 106 and the center cam 112 may both have a plurality of holes 144 and the prosthetic limb connection may have at least one pin 146 configured to extend into the holes 144 on the lower connector 106 and the center cam 112 to rotationally fix the lower connector 106 with respect to the center cam 112 (see FIGS. 17-20). As another example, the center cam 112 may have a cavity configured to receive a protruding face on the upper surface 142 of the lower connector 106. As will be apparent to one of skill in the art, the cavity and the protruding face could be switched so that the cavity is on the upper surface 142 of the lower connector 106 and the protruding face is on the center cam 112. An edge of the cavity may be configured to conform to an edge of the protruding face. Additionally, the edges of the cavity and the protruding face may have a repeating shape, such as a wave pattern or a tooth pattern, to allow them to mate in a plurality of configurations, similar to the plurality of ridges 124 and the plurality of grooves 116 described above. The pattern may complete a full circle or may only extend around a portion of the cavity and the protruding face. Thus, the cavity and the protruding face allow the lower connector 106 to be positioned and rotationally fixed with respect to the center cam 112 in a plurality of configurations to allow for orientation adjustment of the lower connector 106 and thus the prosthetic limb. In embodiments with a lower connector 107, the lower connector 107 may have any of the same features and may be configured to be rotationally fixed with respect to the center cam 112 in the same way. Additionally, although the lower connector 107 is shown in FIG. 18 as comprising two pieces that mate together as discussed in more detail below, it will be understood by a person of skill in the art that the lower connector 107 may also be formed from one integral piece and therefore not have the base 152 and main body 154 with the interlocking radial ridges 160.

Figure 17:
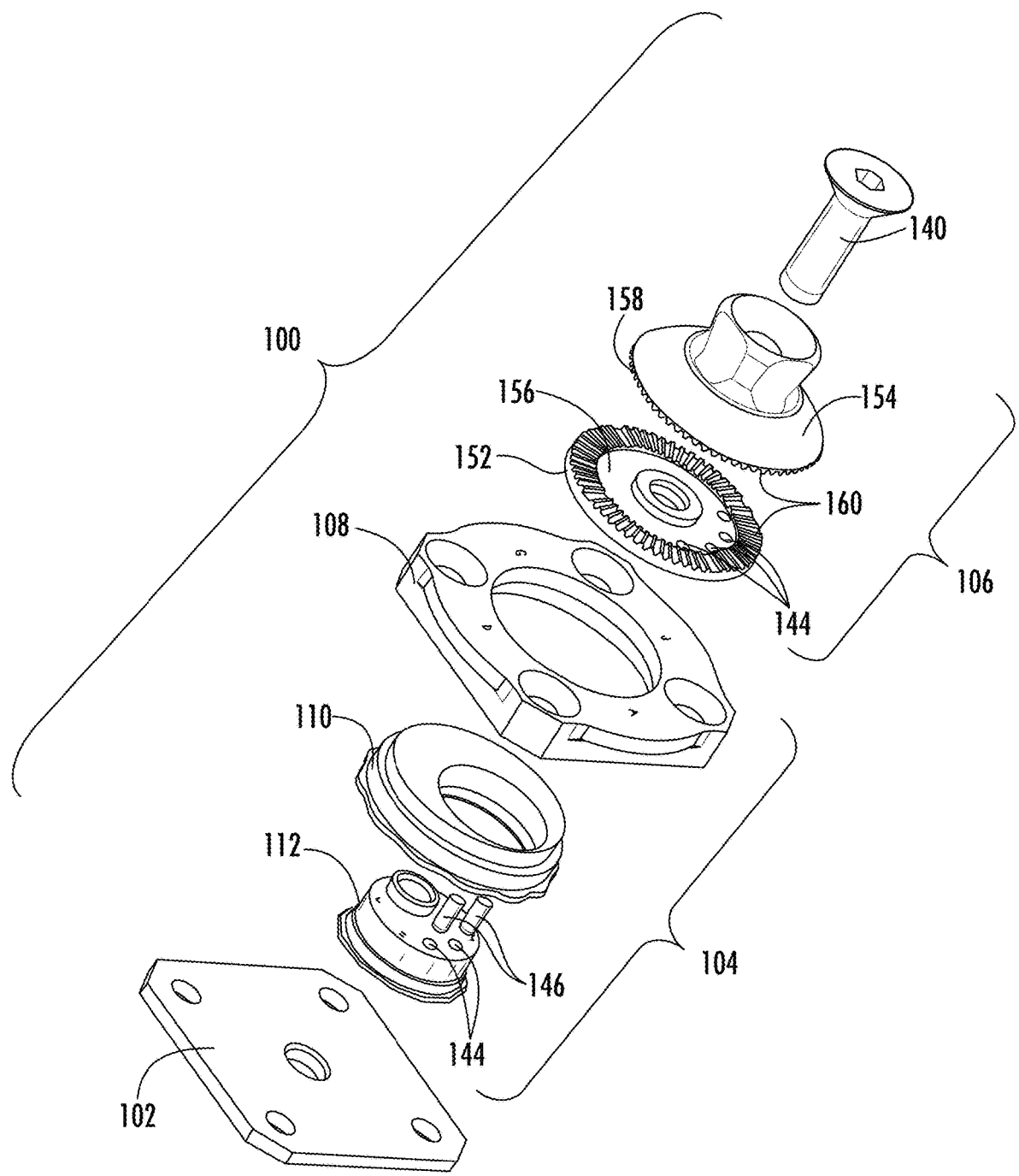
FIG. 17 is an exploded view of an adjustable prosthetic limb connection with an adjustable pyramid mount according to some implementations.

In some implementations, such as those illustrated in FIGS. 17 and 18, the lower connector 106 is split into a base 152 and a main body 154. The base 152 and the main body 154 are configured to interface with each other to be rotationally fixed with respect to each other when pressed together. For example, in some implementations, the base 152 has a bottom surface 156 that is configured to interface with an upper surface 158 of the main body 154 such that, when pressed together, the main body 154 is rotationally fixed with respect to the base 152. In some implementations, each of the bottom surface 156 of the base 152 and the upper surface 158 of the main body 154 has a plurality of radial ridges 160. The radial ridges 160 on the bottom surface 156 of the base 152 are configured to interlock with the radial ridges 160 on the upper surface 158 such that, when pressed together, the main body 154 is rotationally fixed with respect to the base 152. This allows the rotational position of the main body 154 with respect to the base 152 to be adjusted because the main body 154 can interlock with the base 152 in multiple orientations. This provides further adaptability to the prosthetic limb connection 100 by allowing the orientation of the lower connector 106 to be adjusted as needed.

In some implementations, the lower connector 106 is a pyramid-type connector such as those shown in FIGS. 1-3, 17, 19, and 20 and may be configured to insert into a receiver on the prosthetic limb (not shown). In some implementations, the lower connector 106 may be replaced by lower connector 107, which is a pyramid receiver-type connector such as is shown in FIG. 18 and may be configured to receive a projection from the prosthetic limb (not shown). Thus, multiple types of lower connectors 106, 107 are contemplated and could be implemented without affecting the function of the prosthetic limb connection 100.

With reference to FIGS. 21-31, the present disclosure is also related to a prosthetic limb connection 200 that has a mounting plate 102, an alignment mechanism 204, and a lower connector 106. The prosthetic limb connection 200 is in many respects the same as the prosthetic limb connection 100 disclosed above with reference to FIGS. 1-20, and may have any of the features described above regarding the prosthetic limb connection 100. Therefore, as discussed above, the mounting plate 102 is configured to attach to a prosthetic limb socket of a user and the lower connector 106 is configured to attach to a prosthetic limb. The lower connector 106 is also configured to attach to the alignment mechanism 204.

The prosthetic limb connection 200 has an alignment mechanism 204 which is configured to allow adjustment of the alignment of the lower connector 106 with respect to the mounting plate 102 with at least two degrees of freedom, as described above. For the prosthetic limb connection 200, these two degrees of freedom are created by an adjustment of linear position, as described in more detail below.

Figure 21:
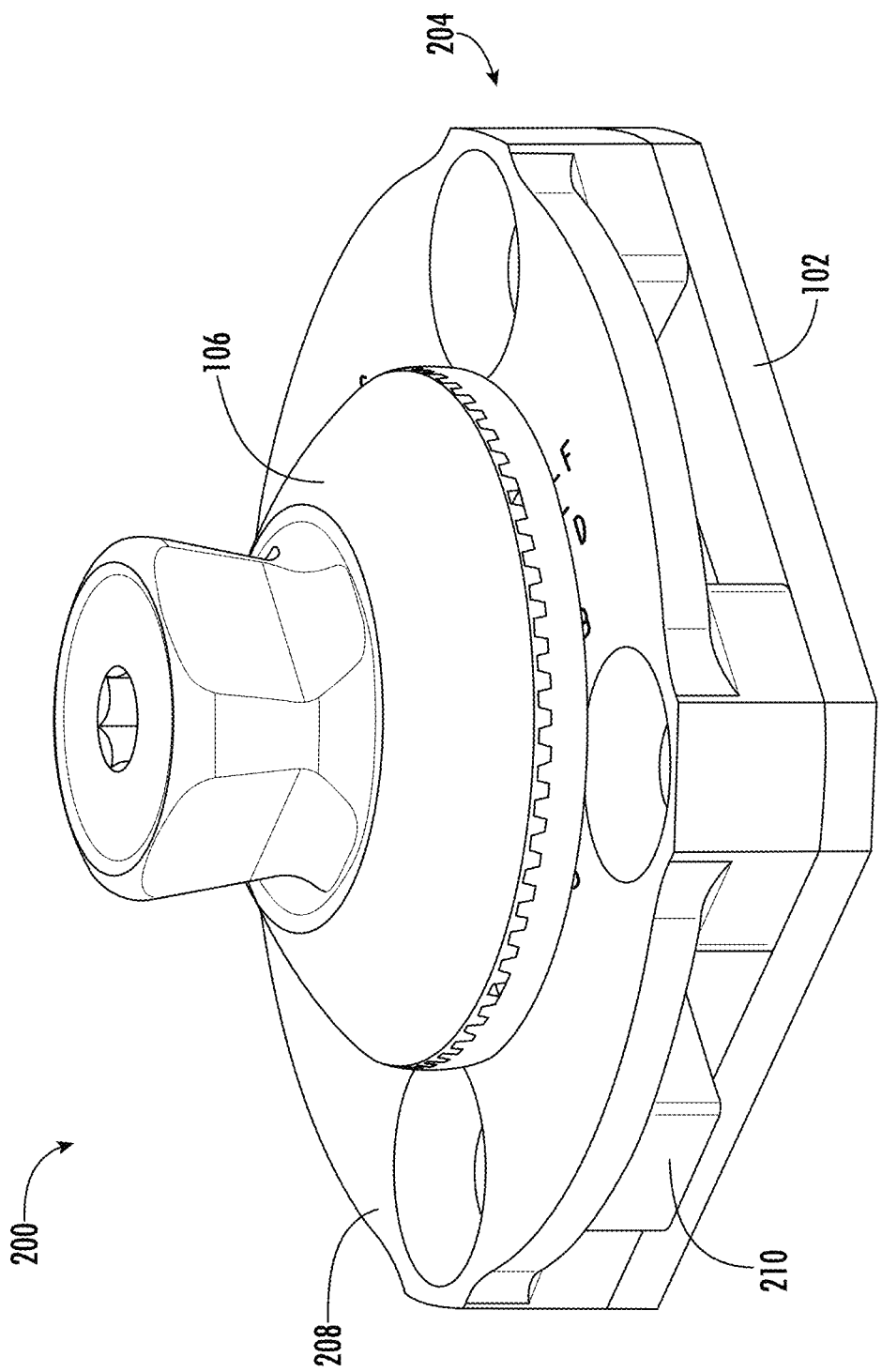
FIG. 21 is a perspective view of an adjustable prosthetic limb connection according to some implementations.
Figure 22:
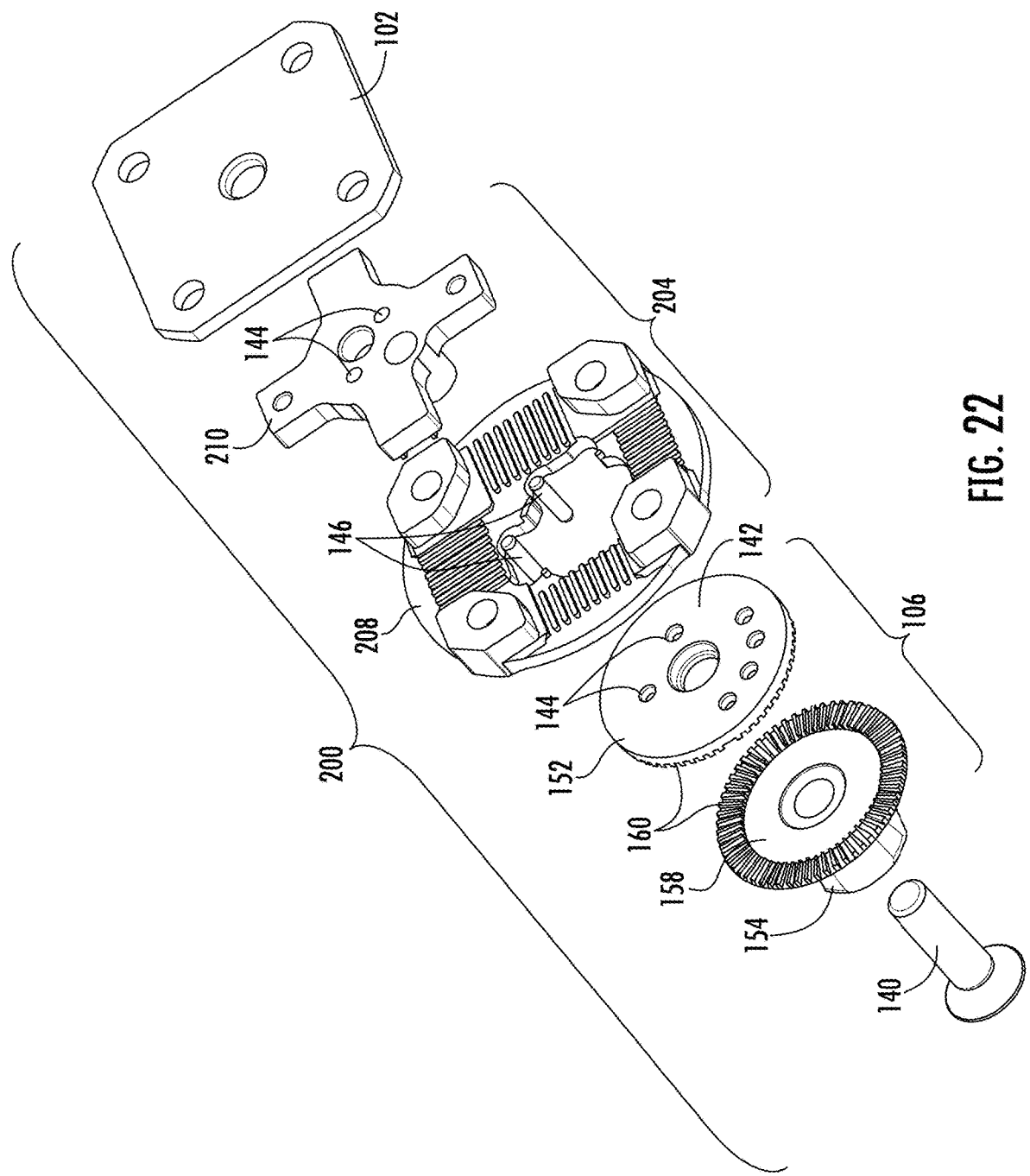
FIG. 22 is a top exploded view of an adjustable prosthetic limb connection according to some implementations.
Figure 23:
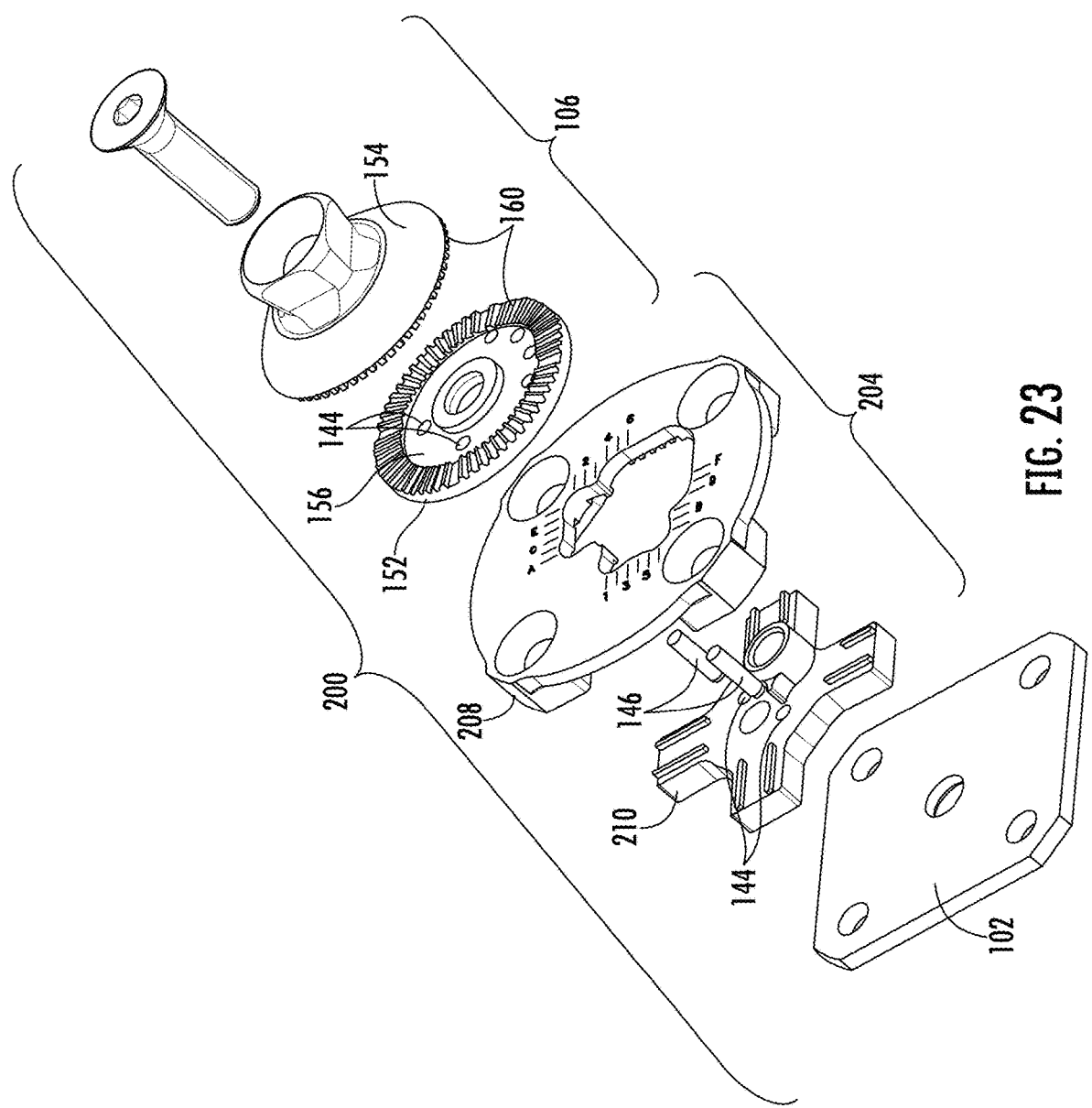
FIG. 23 is a bottom exploded view of an adjustable prosthetic limb connection according to some implementations.

One embodiment of the prosthetic limb connection 200 is illustrated in FIGS. 21-23. As will be apparent to one of skill in the art, although FIGS. 21-23 only show lower connector 106, the lower connector 106 can be replaced with lower connector 107 as desired. (see, e.g., FIG. 18). Thus, either lower connector 106, which is a pyramid-type connector, or lower connector 107, which is a pyramid receiver-type connector, can be implemented with the prosthetic limb connection 200. Similarly, it will be apparent to one of skill in the art that, while FIGS. 21-23 depict the lower connector 106 as being split into a base 152 and a main body 154, as described in more detail above, making the rotational position of the lower connector 106 adjustable, the lower connector 106 may also be formed as one piece like the lower connector 106 shown in FIGS. 1-5.

It will also be apparent to one of skill in the art that the mounting plate 102 that is illustrated in FIGS. 21-23 with respect to the prosthetic limb connection 200 could be replaced with the mounting plate 103 discussed above. (see, e.g., FIG. 19). Thus, while FIGS. 21-23 illustrate a prosthetic limb connection 200 with a mounting plate 102, it is to be understood that the mounting plate 103 could be used to the same effect, and a person of skill in the art will understand situations where the mounting plate 103 should be used instead, such as when the prosthetic limb connection 200 is to be attached to a pin-suction mount. Anytime within this disclosure that the mounting plate 102 is mentioned, it is to be understood that the mounting plate 103 could be used instead.

As mentioned above, the prosthetic limb connection 200 may comprise an alignment mechanism 204 that is configured to couple with the mounting plate 102. The alignment mechanism 204 is also configured to allow adjustment of the alignment of the lower connector 106 with respect to the mounting plate 102 with at least two linear degrees of freedom.

Figure 24:
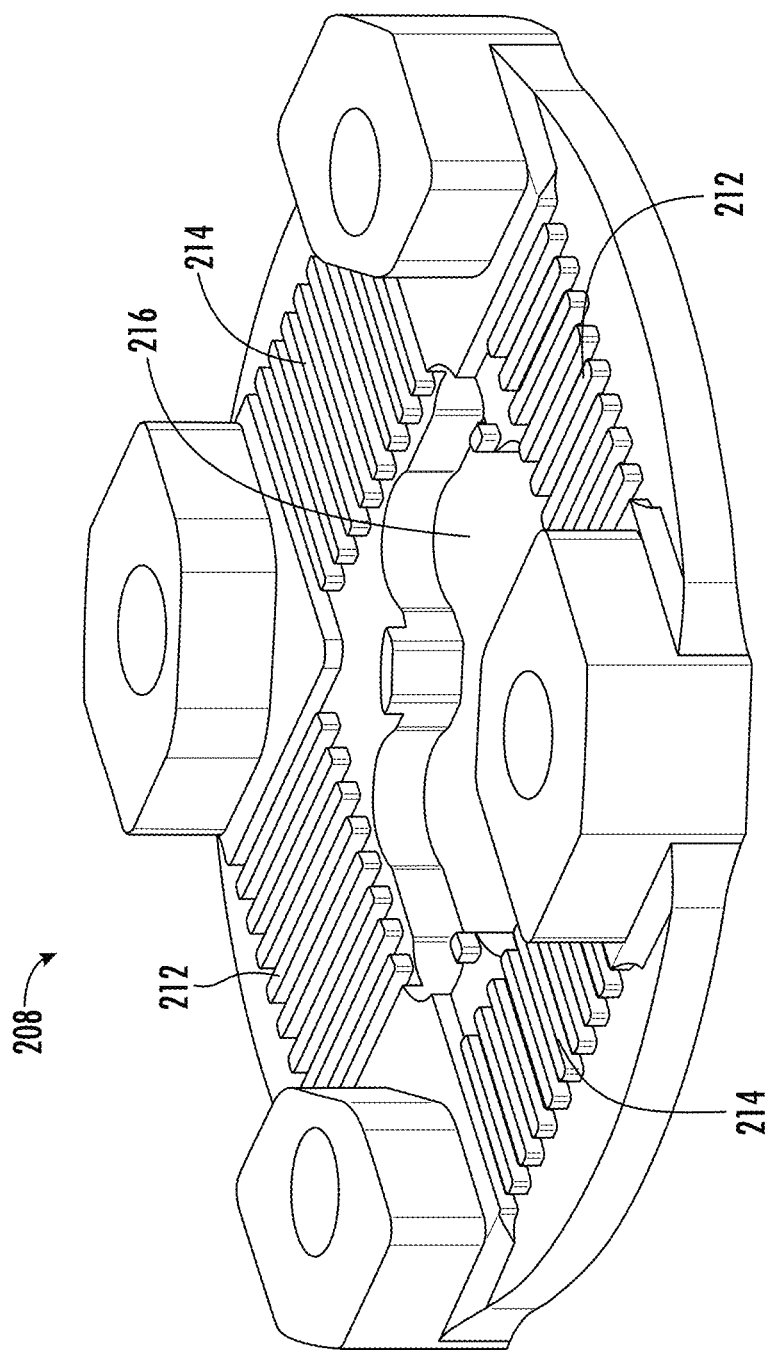
FIG. 24 is a top perspective view of a base plate of an adjustable prosthetic limb connection according to some implementations.
Figure 25:
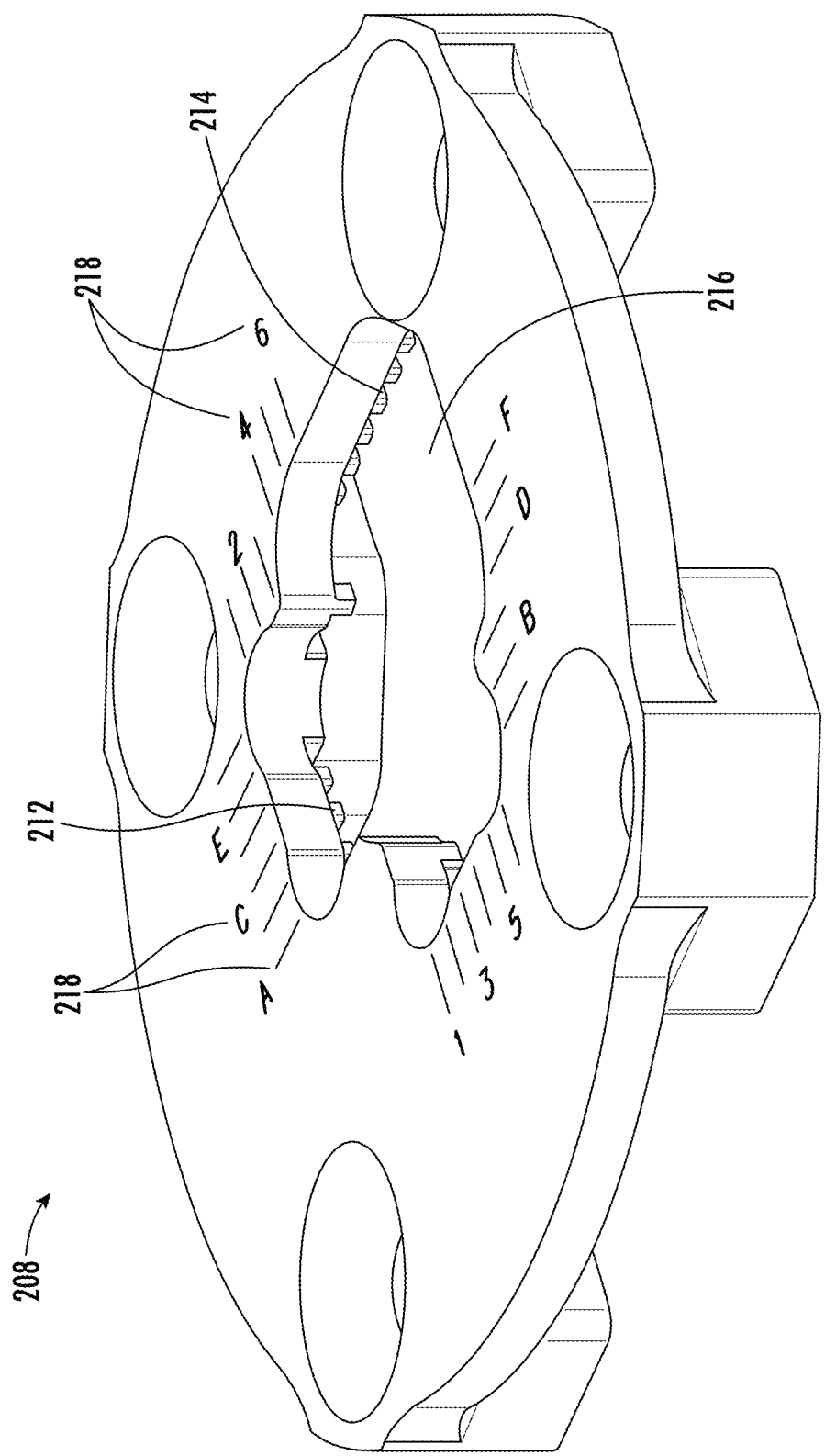
FIG. 25 is a bottom perspective view of a base plate of an adjustable prosthetic limb connection according to some implementations.
Figure 26:
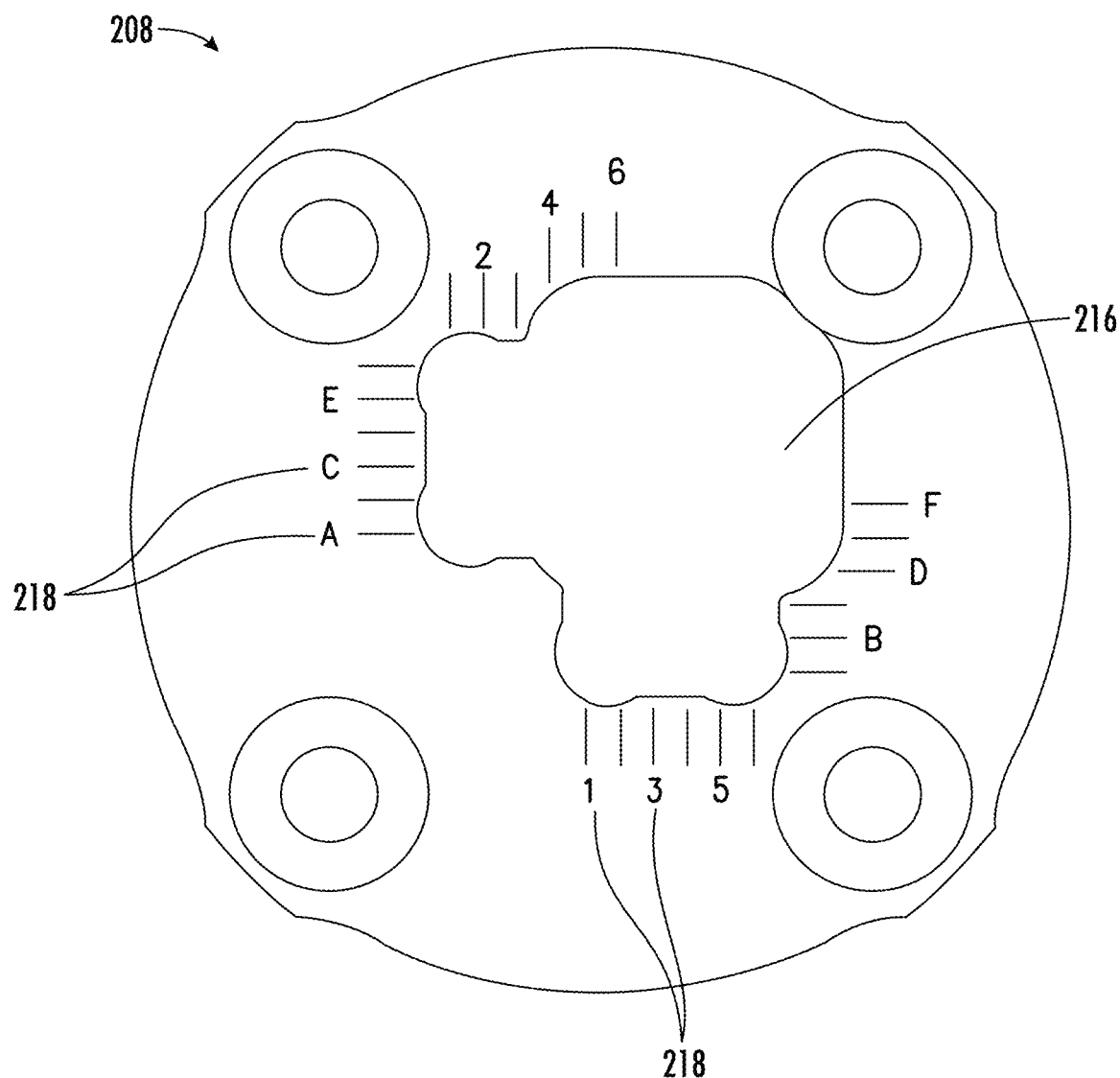
FIG. 26 is a bottom view of a base plate of an adjustable prosthetic limb connection according to some implementations.

The alignment mechanism 204 may comprise a base plate 208 and a linear slide 210. As shown in FIGS. 24-26, the base plate 208 is configured to be secured against the mounting plate 102 and may have a first row of teeth 212 and a second row of teeth 214. In some embodiments, the second row of teeth 214 is arranged perpendicular to the first row of teeth 212. The base plate 208 may have a central aperture 216 configured to allow access to the linear slide 210 through the base plate 208 so that the lower connector 106 can connect to the linear slide 210 while the linear slide 210 is positioned between the base plate 208 and the mounting plate 102. The base plate 208 may also have a plurality of label markings 218 configured to align with the first row of teeth 212 and/or the second row of teeth 214 and indicate a position of the linear slide 210 with respect to the base plate 208 as explained in more detail below.

Figure 27:
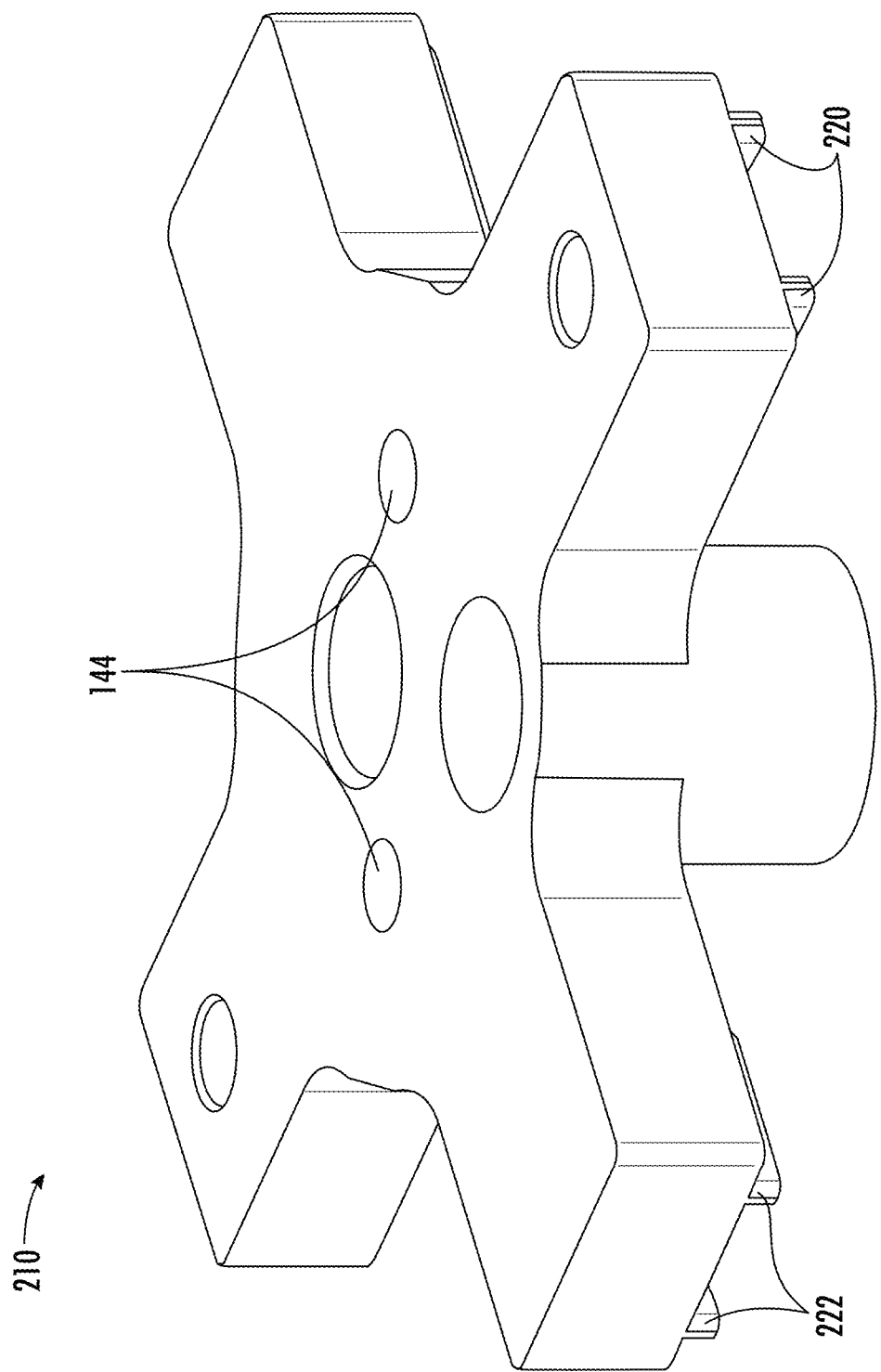
FIG. 27 is a top perspective view of a linear slide of an adjustable prosthetic limb connection according to some implementations.
Figure 28:
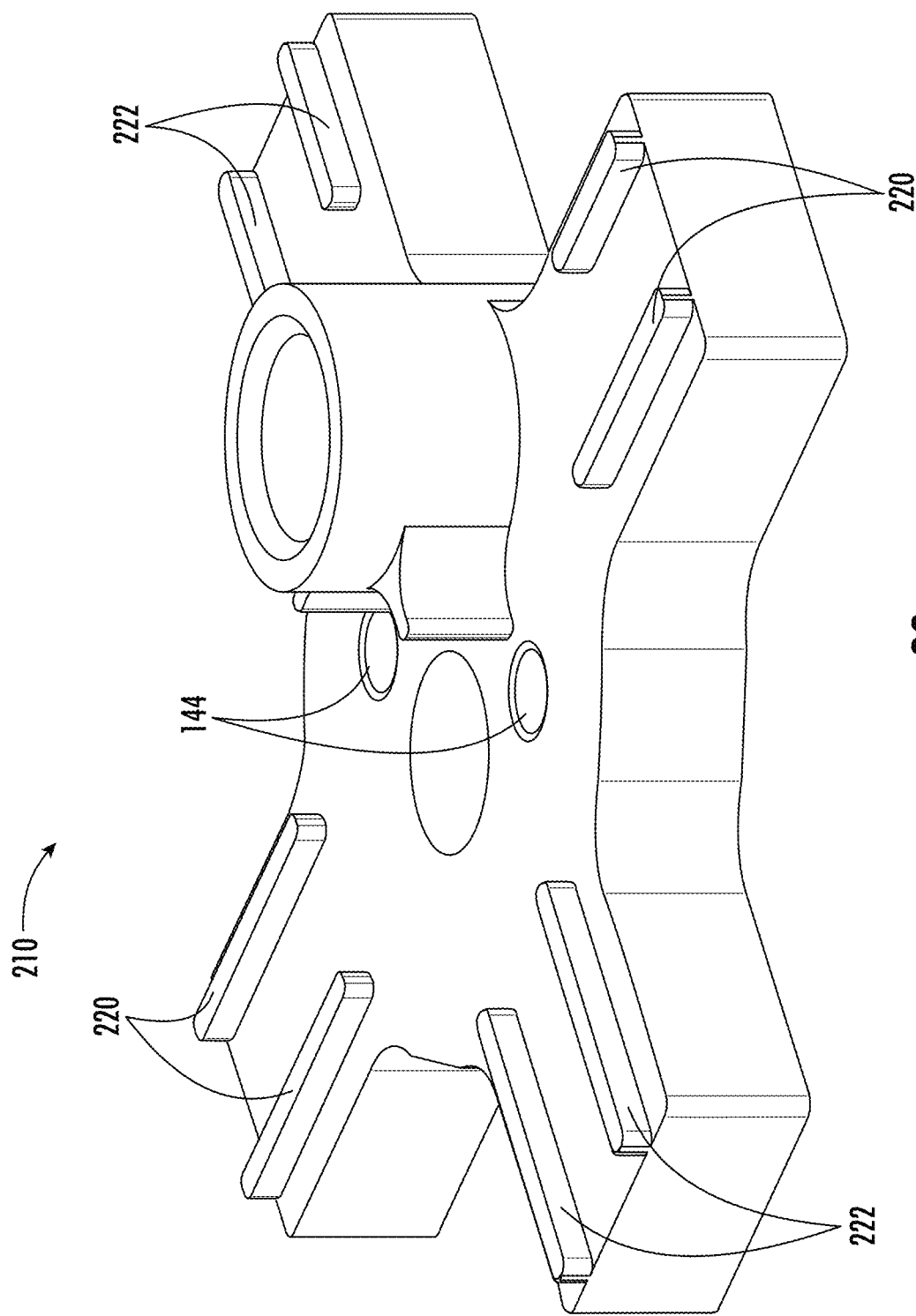
FIG. 28 is a bottom perspective view of linear slide of an adjustable prosthetic limb connection according to some implementations.
Figure 29:
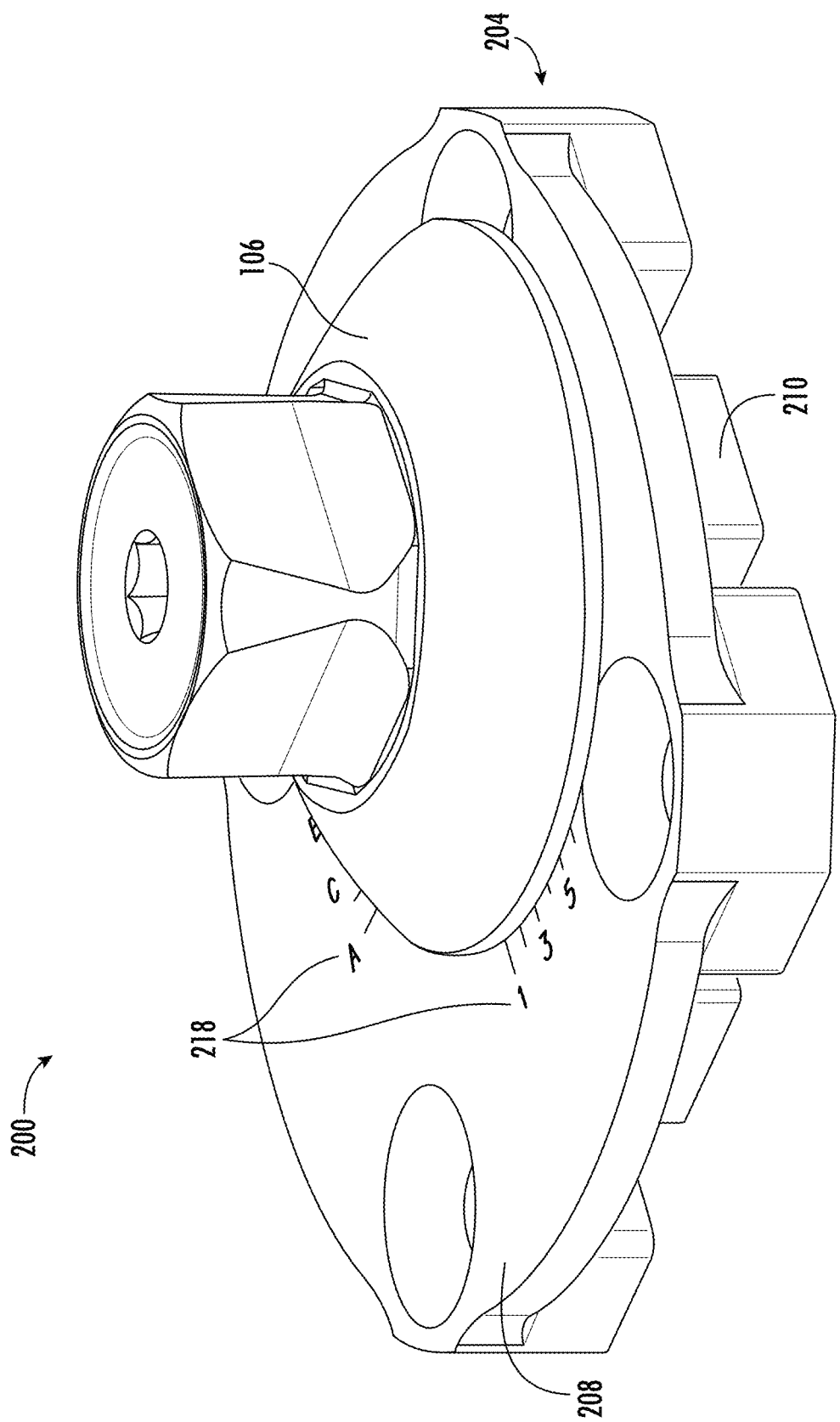
FIG. 29 is a perspective view of an adjustable prosthetic limb connection according to some implementations in the C4 position.
Figure 30:
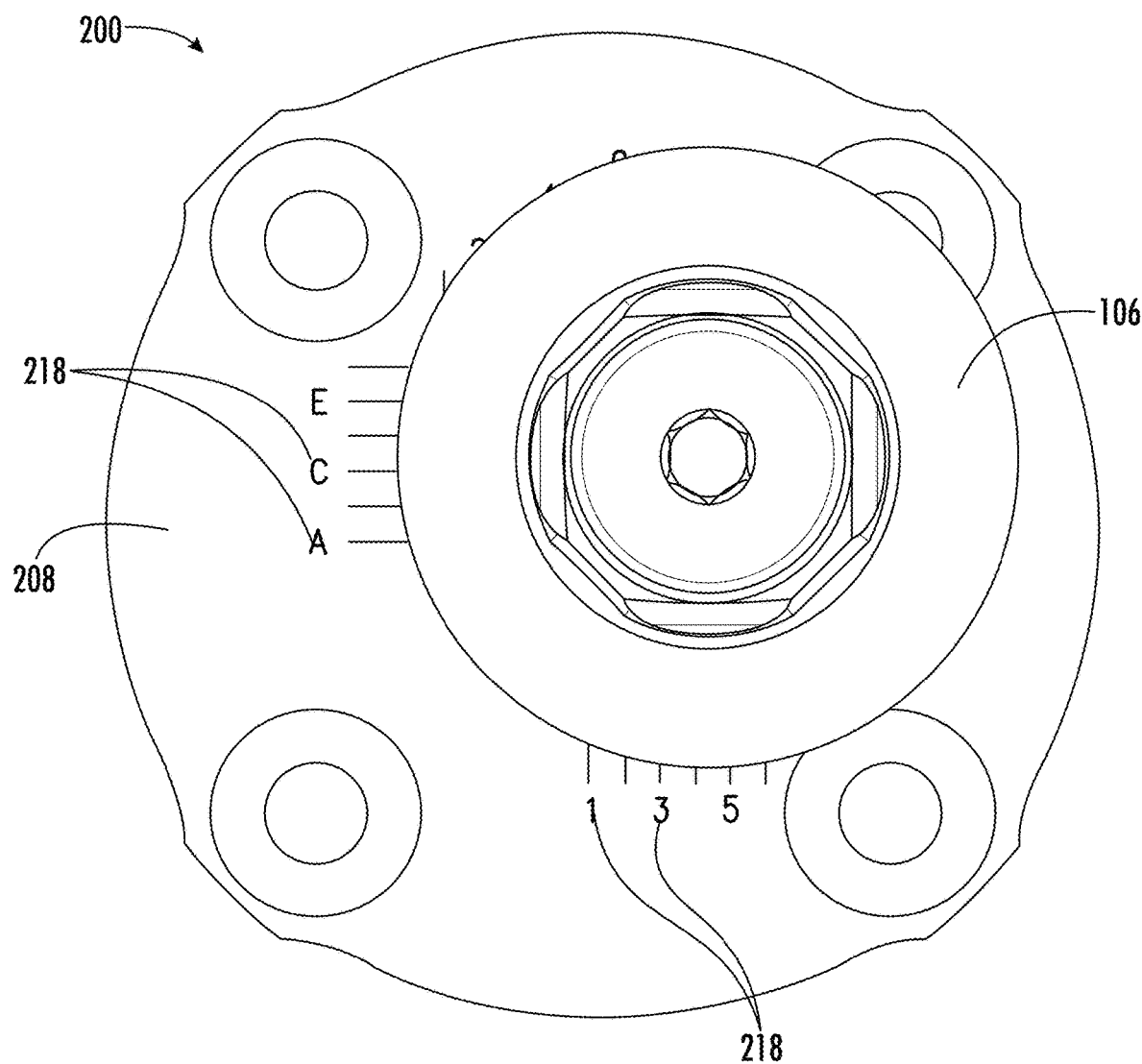
FIG. 30 is a bottom view of an adjustable prosthetic limb connection according to some implementations in the C4 position.

The linear slide 210 may be positioned between the base plate 208 and the mounting plate 102. As shown in FIGS. 27-28, the linear slide 210 may have at least one first ridge 220 and at least one second ridge 222. In some embodiments, the linear slide 210 only has one first ridge 220 and/or second ridge 222, but in other embodiments, the linear slide 210 may have any number of first ridges 220 and/or second ridges 222. For example, in a particular embodiment, the linear slide 210 has two first ridges 220 and two second ridges 222. The number of first ridges 220 may not be equal to the number of second ridges 222. The first ridge 220 is configured to interface with the first row of teeth 212 on the base plate 208 and the second ridge 222 is configured to interface with the second row of teeth 214. In some embodiments, the first ridge 220 is configured to interlock with the first row of teeth 212 and the second ridge 222 is configured to interlock with the second row of teeth 214. When the first ridge 220 and the second ridge 222 interface with the first row of teeth 212 and the second row of teeth 214, the position of the linear slide 210 with respect to the base plate 208 is fixed. Thus, a user can position the linear slide 210 in a desired position with respect to the base plate 208 and then interface the first ridge 220 and the second ridge 222 with the first row of teeth 212 and the second row of teeth 214 to lock the linear slide 210 in the desired position. In this way, the alignment mechanism 204 may be configured to allow adjustment of the alignment of the lower connector 106 with respect to the mounting plate 102 with at least two linear degrees of freedom through adjustment of the at least one first ridge 220 with respect to the first row of teeth 212 and the at least one second ridge with respect to the second row of teeth 214. As shown in FIGS. 29 and 30, the user may use the plurality of label markings 218 as a visual reference for determining the position of the linear slide 210 with respect to the base plate 208. In some implementations, the linear slide 210 may be positioned in any of the positions illustrated in FIG. 31.

In some implementations, the lower connector 106 has an upper surface 142 (see, e.g., FIG. 2) that is configured to interface with the linear slide 210 and rotationally fix the lower connector 106 with respect to the linear slide 210. This allows the lower connector 106, after being positionally adjusted using the alignment mechanism 204 to properly align the line of force through the prosthetic limb, to also be rotationally adjusted to orient the prosthetic limb in the appropriate direction. The lower connector 106 may interface with the linear slide 210 in a variety of ways. FIGS. 22 and 27-28 illustrate several non-limiting examples of the variety of ways the lower connector 106 may interface with the linear slide 210. For example, the lower connector 106 and linear slide 210 may both have a plurality of holes 144 and the prosthetic limb connection may have at least one pin 146 configured to extend into the holes 144 on the lower connector 106 and linear slide 210 to rotationally fix the lower connector 106 with respect to the linear slide 210. In embodiments where the lower connector 106 is split into a base 152 and a main body 154, the holes 144 may extend only through the base 152, leaving the main body 154 to be rotationally adjusted as needed.

The base plate 208 is fixed with respect to the mounting plate 102 and the lower connector 106 is linearly fixed with respect to the linear slide 210. Thus, the alignment of the lower connector 106 with respect to the mounting plate 102 can be adjusted by moving the linear slide 210 with respect to the base plate 208. In this way, the adjustment mechanism 204 can be adjusted to move the lower connector 106 to a new desired position, allowing the alignment of the line of force to be adjusted to properly place the line of force and allow the amputee to return to previous levels of mobility and activity. In some embodiments, the adjustment mechanism 204 is configured to allow adjustment in one quadrant. This allows the device to be smaller in size. If the user requires adjustment in a different quadrant, the adjustment mechanism 204 can be detached and rotated to allow adjustment in the required quadrant. FIG. 31 illustrates potential positions for the lower connector 106 in one quadrant when implemented with the adjustment mechanism 204. As noted, a different quadrant can be selected by orienting the adjustment mechanism 204 in the desired quadrant. As mentioned above, the simplicity of this adjustment is a significant improvement over the current process of repeatedly refitting the amputee with new sockets each time an adjustment is required. Using the prosthetic limb connection 200 disclosed herein, a prosthetist can adjust the prosthetic limb to a new position in just a few minutes.

The prosthetic limb connection 100 and the prosthetic limb connection 200 described herein allow adjustment with two linear degrees of freedom in the transverse plane while keeping within a small volume and using a small amount of material to reduce weight of the prosthetic limb connection 100 and the prosthetic limb connection 200. Additionally, the prosthetic limb connection 100 and the prosthetic limb connection 200 can work with any current suspension system and do not require any modifications to the socket to incorporate adjustment. The prosthetic limb connection 100 and the prosthetic limb connection 200 also require less space in the build height than current systems, which increases the number of prosthetic feet that an amputee can choose from. In some implementations, the prosthetic limb connection 100 and the prosthetic limb connection 200 are made from aluminum, stainless steel, or titanium to provide needed strength and corrosion resistance and avoid too much weight. Weight constraints favor aluminum and titanium while cost constraints favor aluminum and stainless steel. Strength constraints favor titanium and stainless steel. Other materials that would be beneficial for these characteristics will be apparent to one of skill in the art and are contemplated by this disclosure.

Many additional implementations are possible. Further implementations are within the CLAIMS.

It will be understood that implementations of the prosthetic limb connection include but are not limited to the specific components disclosed herein, as virtually any components consistent with the intended operation of various prosthetic limb connections may be utilized. Accordingly, for example, it should be understood that while the drawings and accompanying text show and describe particular prosthetic limb connection implementations, any such implementation may comprise any shape, size, style, type, model, version, class, grade, measurement, concentration, material, weight, quantity, and/or the like consistent with the intended operation of prosthetic limb connections.

The concepts disclosed herein are not limited to the specific prosthetic limb connections shown herein. For example, it is specifically contemplated that the components included in particular prosthetic limb connections may be formed of any of many different types of materials or combinations that can readily be formed into shaped objects and that are consistent with the intended operation of prosthetic limb connections. For example, the components may be formed of: rubbers (synthetic and/or natural) and/or other like materials; glasses (such as fiberglass), carbon-fiber, aramid-fiber, any combination therefore, and/or other like materials; elastomers and/or other like materials; polymers such as thermoplastics (such as ABS, fluoropolymers, polyacetal, polyamide, polycarbonate, polyethylene, polysulfone, and/or the like, thermosets (such as epoxy, phenolic resin, polyimide, polyurethane, and/or the like), and/or other like materials; plastics and/or other like materials; composites and/or other like materials; metals, such as zinc, magnesium, titanium, copper, iron, steel, carbon steel, alloy steel, tool steel, stainless steel, spring steel, aluminum, and/or other like materials; and/or any combination of the foregoing.

Furthermore, prosthetic limb connections may be manufactured separately and then assembled together, or any or all of the components may be manufactured simultaneously and integrally joined with one another. Manufacture of these components separately or simultaneously, as understood by those of ordinary skill in the art, may involve 3-D printing, extrusion, pultrusion, vacuum forming, injection molding, blow molding, resin transfer molding, casting, forging, cold rolling, milling, drilling, reaming, turning, grinding, stamping, cutting, bending, welding, soldering, hardening, riveting, punching, plating, and/or the like. If any of the components are manufactured separately, they may then be coupled or removably coupled with one another in any manner, such as with adhesive, a weld, a fastener, any combination thereof, and/or the like for example, depending on, among other considerations, the particular material(s) forming the components.

In places where the description above refers to particular prosthetic limb connection implementations, it should be readily apparent that a number of modifications may be made without departing from the spirit thereof and that these implementations may be applied to other implementations disclosed or undisclosed. The presently disclosed prosthetic limb connections are, therefore, to be considered in all respects as illustrative and not restrictive.

I claim:

1. An adjustable prosthetic limb connection, comprising:
a mounting plate configured to attach to a prosthetic limb socket of a user;
an alignment mechanism configured to couple with the mounting plate, the alignment mechanism comprising:
a base plate in contact with and secured against the mounting plate, the base plate having a first row of elongated teeth, a second row of elongated teeth arranged perpendicular to the first row of elongated teeth, and a central aperture extending through the base plate, wherein a center of the central aperture is offset from a center of the base plate, wherein the central aperture is positioned at an intersection between the first row of elongated teeth and the second row of elongated teeth, and wherein the first row of elongated teeth and the second row of elongated teeth are positioned adjacent to an outer circumference of the base plate; and
a linear slide positioned between the base plate and the mounting plate, the linear slide shaped as a cross, the linear slide having at least one first ridge and at least one second ridge configured to interface with the first row of elongated teeth of the base plate and with the second row of elongated teeth of the base plate, respectively, such that the at least one first ridge is configured to interlock with the first row of elongated teeth and the at least one second ridge is configured to interlock with the second row of elongated teeth, wherein a total number of ridges of the at least one first ridge and a total number of ridges of the at least one second ridge are respectively less than a total number of teeth of the first row of elongated teeth and a total number of teeth of the second row of elongated teeth; and
a lower connector configured to attach to the linear slide of the alignment mechanism through the central aperture of the base plate, and configured to attach to a prosthetic limb;
wherein the alignment mechanism is configured to allow adjustment of the alignment of the lower connector with respect to the mounting plate within a first quadrant of an available adjustment space with at least two linear degrees of freedom through adjustment of the at least one first ridge with respect to the first row of elongated teeth and the at least one second ridge with respect to the second row of elongated teeth; and
wherein the alignment mechanism is configured to rotate to a plurality of positions, wherein in each of the plurality of positions, the adjustment of the alignment of the lower connector with respect to the mounting plate occurs in a different quadrant of the available adjustment space due to the central aperture offset.

2. The adjustable prosthetic limb connection of claim 1, wherein the lower connector comprises a base and a main body separate from the base, wherein a bottom surface of the base is configured to interface with an upper surface of the main body to rotationally fix the main body with respect to the base.

3. The adjustable prosthetic limb connection of claim 2, wherein each of the bottom surface of the base and the upper surface of the main body has a plurality of radial ridges and wherein the pluralities of radial ridges on the bottom surface of the base and the upper surface of the main body allow a rotational position of the main body with respect to the base to be adjusted.

4. An adjustable prosthetic limb connection, comprising:
a mounting plate configured to attach to a prosthetic limb socket of a user;
an alignment mechanism configured to couple with the mounting plate, the alignment mechanism comprising:
a base plate configured to be secured against the mounting plate, the base plate having a first row of teeth, a second row of teeth, and a central aperture extending through the base plate, wherein a center of the central aperture is offset from a center of the base plate; and
a linear slide positioned between the base plate and the mounting plate and configured to interface with the base plate, the linear slide having at least one first ridge and at least one second ridge configured to interface with the first row of teeth of the base plate and with the second row of teeth of the base plate, respectively; and
a lower connector configured to attach to the alignment mechanism and to a prosthetic limb;
wherein the alignment mechanism is configured to allow adjustment of the alignment of the lower connector with respect to the mounting plate within a first quadrant of an available adjustment space with at least two linear degrees of freedom through adjustment of the at least one first ridge with respect to the first row of teeth and the at least one second ridge with respect to the second row of teeth; and
wherein the alignment mechanism is configured to rotate to a plurality of positions, wherein in each of the plurality of positions the adjustment of the alignment of the lower connector with respect to the mounting plate occurs in a different quadrant of the available adjustment space due to the central aperture offset.

5. The adjustable prosthetic limb connection of claim 4, wherein the lower connector comprises a base and a main body separate from the base, wherein a bottom surface of the base is configured to interface with an upper surface of the main body to rotationally fix the main body with respect to the base.

6. The adjustable prosthetic limb connection of claim 5, wherein each of the bottom surface of the base and the upper surface of the main body has a plurality of radial ridges and wherein the pluralities of radial ridges on the bottom surface of the base and the upper surface of the main body allow a rotational position of the main body with respect to the base to be adjusted.

7. The adjustable prosthetic limb connection of claim 4, wherein the at least two linear degrees of freedom are in a transverse plane and wherein the prosthetic limb is configured to be perpendicular to the transverse plane.

8. The adjustable prosthetic limb connection of claim 4, wherein the central aperture is positioned at an intersection between the first row of teeth and the second row of teeth.

9. The adjustable prosthetic limb connection of claim 4, wherein the first row of teeth and the second row of teeth are positioned adjacent to an outer circumference of the base plate.

10. The adjustable prosthetic limb connection of claim 4, wherein the linear slide is shaped as a cross.

11. The adjustable prosthetic limb connection of claim 4, wherein a total number of ridges of the at least one first ridge and a total number of ridges of the at least one second ridge are respectively less than a total number of teeth of the first row of teeth and a total number of teeth of the second row of teeth.

12. An adjustable prosthetic limb connection, comprising:
a mounting plate configured to attach to a prosthetic limb socket of a user;
an alignment mechanism configured to couple with the mounting plate, the alignment mechanism comprising:
  a base plate configured to be secured against the mounting plate, the base plate having a first row of teeth, a second row of teeth, and a central aperture extending through the base plate, wherein a center of the central aperture is offset from a center of the base plate; and
  a linear slide positioned between the base plate and the mounting plate and configured to interface with the base plate, the linear slide having at least one first ridge and at least one second ridge configured to interface with the first row of teeth of the base plate and with the second row of teeth of the base plate, respectively; and
a lower connector configured to attach to the alignment mechanism and to a prosthetic limb;
wherein the alignment mechanism is configured to allow adjustment of the alignment of the lower connector with respect to the mounting plate within a first region of an available adjustment space with at least two linear degrees of freedom; and
wherein the alignment mechanism is configured to rotate to a plurality of positions, wherein in each of the plurality of positions the adjustment of the alignment of the lower connector with respect to the mounting plate occurs in a different region of the available adjustment space.

13. The adjustable prosthetic limb connection of claim 12, wherein the alignment mechanism is configured to allow adjustment of the alignment of the lower connector with respect to the mounting plate through adjustment of the linear slide with respect to the base plate.

14. The adjustable prosthetic limb connection of claim 12, further comprising a plurality of pins configured to engage with the lower connector and with the alignment mechanism to rotationally fix the lower connector with respect to the alignment mechanism.

15. The adjustable prosthetic limb connection of claim 12, wherein the lower connector comprises a base and a main body separate from the base, wherein a bottom surface of the base is configured to interface with an upper surface of the main body to rotationally fix the main body with respect to the base.

16. The adjustable prosthetic limb connection of claim 12, wherein the at least two linear degrees of freedom are in a transverse plane and wherein the prosthetic limb is configured to be perpendicular to the transverse plane.

17. The adjustable prosthetic limb connection of claim 12, wherein the central aperture is positioned at an intersection between the first row of teeth and the second row of teeth.

18. The adjustable prosthetic limb connection of claim 12, wherein the first row of teeth and the second row of teeth are positioned adjacent to an outer circumference of the base plate.

19. The adjustable prosthetic limb connection of claim 12, wherein the linear slide is shaped as a cross.

20. The adjustable prosthetic limb connection of claim 12, wherein a total number of ridges of the at least one first ridge and a total number of ridges of the at least one second ridge are respectively less than a total number of teeth of the first row of teeth and a total number of teeth of the second row of teeth.

* * * * *